US009589559B2

(12) United States Patent
Zhong et al.

(10) Patent No.: US 9,589,559 B2
(45) **Date of Patent: *Mar. 7, 2017**

(54) METHODS AND SYSTEMS FOR IMPLEMENTING BONE CONDUCTION-BASED NOISE CANCELLATION FOR AIR-CONDUCTED SOUND

(71) Applicant: Google Inc., Mountain View, CA (US)

(72) Inventors: Xuan Zhong, Cupertino, CA (US); Jianchun Dong, Palo Alto, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/089,958

(22) Filed: Apr. 4, 2016

(65) Prior Publication Data

US 2016/0217781 A1 Jul. 28, 2016

Related U.S. Application Data

(63) Continuation of application No. 14/060,911, filed on Oct. 23, 2013, now Pat. No. 9,324,313.

(51) Int. Cl.
*A61F 11/06* (2006.01)
*G10K 11/16* (2006.01)
(Continued)

(52) U.S. Cl.
CPC .......... *G10K 11/1788* (2013.01); *G10K 11/24* (2013.01); *H04R 1/028* (2013.01);
(Continued)

(58) Field of Classification Search
CPC .......... H04R 17/00; H04R 1/01; H04R 1/028; G10K 11/1788; G10K 11/24
See application file for complete search history.

(56) References Cited

U.S. PATENT DOCUMENTS 5,740,258 A 4/1998 Goodwin-Johansson
8,325,963 B2 12/2012 Kimura
(Continued)

OTHER PUBLICATIONS

Van Den Bogaert et al., Horizontal localization with bilateral hearing aids: Without is better than with, J. Acoust. Soc. Am., Jan. 2006, pp. 515-526, vol. 119, No. 1, U.S.A.
(Continued)

*Primary Examiner* — Regina N Holder
(74) *Attorney, Agent, or Firm* — McDonnell Boehnen Hulbert & Berghoff LLP

(57) ABSTRACT

A wearable computing device can receive, via at least one input transducer, a first audio signal associated with ambient sound from an environment of the device. The device can then process the first audio signal so as to determine a second audio signal that is out of phase with the first audio signal and effective to substantially cancel at least a portion of the first audio signal. The device may then generate a noise-cancelling audio signal based on the second audio signal, based on a third audio signal, and based on one or more wearer-specific parameters, where the third audio signal is representative of a sound to be provided by the device. The device may then cause a bone conduction transducer (BCT) to vibrate so as to provide to an ear a noise-cancelling sound effective to substantially cancel at least a portion of the ambient sound.

20 Claims, 14 Drawing Sheets

(51) Int. Cl.

| | |
|---|---|
| ***H03B 29/00*** | (2006.01) |
| ***G10K 11/178*** | (2006.01) |
| ***G10K 11/24*** | (2006.01) |
| ***H04R 1/02*** | (2006.01) |
| ***H04R 1/10*** | (2006.01) |
| ***H04R 17/00*** | (2006.01) |

(52) U.S. Cl.

CPC ............... *H04R 1/10* (2013.01); *H04R 17/00* (2013.01); *G10K 2210/1081* (2013.01); *G10K 2210/1291* (2013.01); *G10K 2210/3229* (2013.01); *H04R 2460/01* (2013.01); *H04R 2460/13* (2013.01)

(56) References Cited

U.S. PATENT DOCUMENTS

| | | | | |
|---|---|---|---|---|
| 8,401,212 | B2 | 3/2013 | Puria et al. | |
| 8,989,417 | B1 * | 3/2015 | Zhong .................... | H04R 5/033 381/312 |
| 9,324,313 | B1 * | 4/2016 | Zhong .................. | G10K 11/175 |
| 2008/0253595 | A1 | 10/2008 | Steinbuss | |
| 2009/0304214 | A1 | 12/2009 | Xiang et al. | |
| 2011/0293105 | A1 | 12/2011 | Arie et al. | |
| 2011/0301729 | A1 | 12/2011 | Heiman et al. | |
| 2012/0300956 | A1 | 11/2012 | Horii | |
| 2013/0051594 | A1 | 2/2013 | Semcken | |
| 2013/0142348 | A1 | 6/2013 | Weisman | |
| 2013/0156202 | A1 * | 6/2013 | Hamacher ............ | H04R 25/453 381/23.1 |

OTHER PUBLICATIONS

Wazen, et al., Localization by unilateral BAHA users, Otolaryngology—Head and Neck Surgery, Jun. 2005, pp. 928-932, vol. 132, No. 6, U.S.A.

Stone et al., Tolerable Hearing Aid Delays, II. Estimation of Limits Imposed During Speech Production, Ear & Hearing, Aug. 2002, pp. 325-338, vol. 23, No. 4, U.S.A.

Stone et al., Tolerable Hearing Aid Delays, I. Estimation of Limits Imposed by the Auditory Path Alone Using Simulated Hearing Losses, Ear & Hearing, Jun. 1999, p. 182, vol. 20, No. 3, U.S.A.

Liao, Application of cross-talk cancellation to the improvement of binaural directional properties for individuals using bone anchored hearing aids (BAHA), Master's Thesis in the Master's programme in Sound and Vibration at Chalmers University of Technology, 2010, Goteborg, Sweden.

* cited by examiner

METHODS AND SYSTEMS FOR IMPLEMENTING BONE CONDUCTION-BASED NOISE CANCELLATION FOR AIR-CONDUCTED SOUND

CROSS-REFERENCE TO RELATED APPLICATION

The present application is a continuation of U.S. patent application Ser. No. 14/060,911, filed on Oct. 23, 2013, and entitled "Methods and Systems for Implementing Bone Conduction-Based Noise Cancellation for Air-Conducted Sound," which is herein incorporated by reference as if fully set forth in this description.

BACKGROUND

Unless otherwise indicated herein, the materials described in this section are not prior art to the claims in this application and are not admitted to be prior art by inclusion in this section.

Computing systems such as personal computers, laptop computers, tablet computers, cellular phones, and countless types of Internet-capable devices are prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a very small image display element close enough to a wearer's (or user's) eye(s) such that the displayed image fills or nearly fills the field of view, and appears as a normal sized image, such as might be displayed on a traditional image display device. The relevant technology may be referred to as "near-eye displays."

Near-eye displays are fundamental components of wearable displays, also sometimes called "head-mounted displays" or "head-mountable devices" (HMDs). A head-mounted display places a graphic display or displays close to one or both eyes of a wearer. To generate the images on a display, a computer processing system may be used. Such displays may occupy part or all of a wearer's field of view. Further, head-mounted displays may be as small as a pair of glasses or as large as a helmet.

SUMMARY

In one aspect, the present application describes a method. The method may comprise receiving, by at least one input transducer coupled to a wearable computing device, a first audio signal associated with ambient sound from an environment of the wearable computing device. The method may also comprise the wearable computing device processing the first audio signal so as to determine a second audio signal that is out of phase with the first audio signal and effective to substantially cancel at least a portion of the first audio signal, the processing being based on one or more wearer-specific parameters. The method may further comprise the wearable computing device generating a noise-cancelling audio signal based on the second audio signal and based on a third audio signal, where the third audio signal is representative of a sound to be provided by the wearable computing device. The method may still further comprise, based on the noise-cancelling audio signal, the wearable computing device causing a bone conduction transducer (BCT) coupled to the wearable computing device to vibrate so as to provide to an ear a noise-cancelling sound representative of the noise-cancelling audio signal and effective to substantially cancel at least a portion of the ambient sound.

In another aspect, the present application describes a non-transitory computer readable medium having stored thereon executable instructions that, upon execution by a wearable computing device, cause the wearable computing device to perform functions. The functions may comprise receiving, by at least one input transducer coupled to the wearable computing device, a first audio signal associated with ambient sound from an environment of the wearable computing device. The functions may also comprise processing the first audio signal so as to determine a second audio signal that is out of phase with the first audio signal and effective to substantially cancel at least a portion of the first audio signal, the processing being based on one or more wearer-specific parameters. The functions may further comprise generating a noise-cancelling audio signal based on the second audio signal and based on a third audio signal, where the third audio signal is representative of a sound to be provided by the wearable computing device. The functions may still further comprise, based on the noise-cancelling audio signal, causing a bone conduction transducer (BCT) coupled to the wearable computing device to vibrate so as to provide to an ear a noise-cancelling sound representative of the noise-cancelling audio signal and effective to substantially cancel at least a portion of the ambient sound.

In yet another aspect, the present application describes a system. The system may comprise a head-mountable device (HMD) and at least one processor coupled to the HMD. The system may also comprise data storage comprising instructions executable by the at least one processor to cause the system to perform functions. The functions may comprise receiving, by at least one input transducer coupled to the HMD, a first audio signal associated with ambient sound from an environment of the HMD. The functions may also comprise processing the first audio signal so as to determine a second audio signal that is out of phase with the first audio signal and effective to substantially cancel at least a portion of the first audio signal, the processing being based on one or more wearer-specific parameters. The functions may further comprise generating a noise-cancelling audio signal based on the second audio signal and based on a third audio signal, wherein the third audio signal is representative of a sound to be provided by the HMD. The functions may still further comprise, based on the noise-cancelling audio signal, causing at least one bone conduction transducer (BCT) coupled to the HMD to vibrate so as to provide to an ear a noise-cancelling sound representative of the noise-cancelling audio signal and effective to substantially cancel at least a portion of the ambient sound.

These as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrative embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Figure 1A:
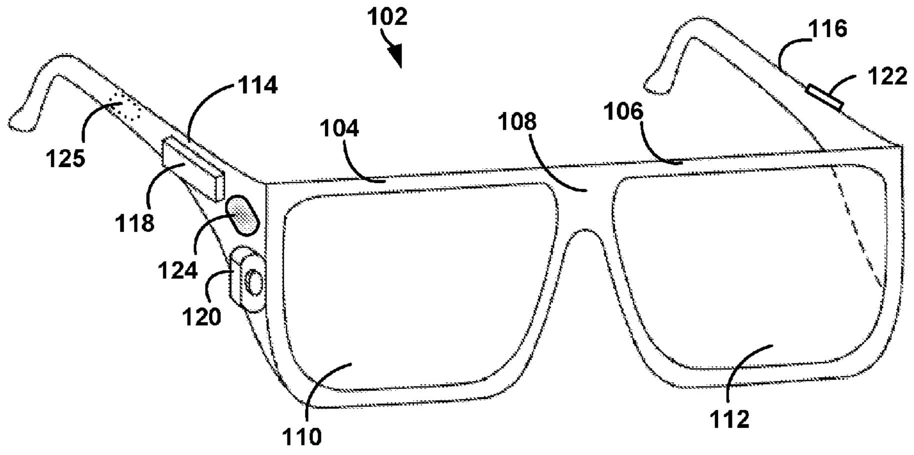
FIG. 1A illustrates a wearable computing system according to at least some embodiments described herein.

Example methods and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. In the following detailed description, reference is made to the accompanying figures, which form a part thereof. In the figures, similar symbols typically identify similar components, unless context dictates otherwise. Other embodiments may be utilized, and other changes may be made, without departing from the scope of the subject matter presented herein.

The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Bone conduction audio can be provided to a wearer of a wearable computing device, such as a head-mountable device (HMD), by a bone conduction transducer (BCT) vibrating the skull of the wearer and propagating bone-conducted sound through the bones and tissues of the wearer's head. However, many BCT-implemented HMDs leave the wearer's ears exposed to unwanted sound (i.e., ambient noise).

As such, disclosed herein is a method for a wearable computing device, such as an HMD, to cancel, or reduce, ambient noise. The HMD may receive, via at least one input transducer such as a microphone, a first audio signal associated with ambient sound from a surrounding environment of the HMD. The at least one input transducer may be coupled to the HMD proximate to a first ear of a wearer of the HMD so as to "pick up" the ambient noise at the first ear of the wearer. The HMD may then process the first audio signal so as to determine a second audio signal that is out of phase with the first audio signal and effective to substantially cancel at least a portion of the first audio signal. The second audio signal may be in anti-phase (e.g., 180 degrees out of phase) with the first audio signal, so as to produce a sound that better reduces the ambient sound. The processing may be performed by a noise-cancelling processor coupled to the HMD.

The HMD may then generate a noise-cancelling audio signal based on the second audio signal and based on a third audio signal that is representative of a sound to be provided by the HMD (e.g., a desired signal intended to be heard by the wearer). The noise-cancelling audio signal may be further based on one or more wearer-specific parameters, the parameters being "wearer-specific" because a given wearer's head may have unique properties unlike other wearer's heads. In some examples, the noise-cancelling audio signal may include a superposition of the second audio signal and the third audio signal.

Based on the noise-cancelling audio signal, the HMD may then cause a first BCT coupled to the HMD to vibrate so as to provide a noise-cancelling sound to the first ear of the wearer, where the noise-cancelling sound is representative of the noise-cancelling audio signal and effective to cancel at least a portion of the ambient sound such that the wearer perceives the sound represented by the third audio signal and perceives substantially none of the ambient sound.

In some examples, the third audio signal may be a signal received from another computing device, such as a voice communication signal received by a smartphone or other computing device that is in communication with the HMD. In other examples, the third audio signal may be generated by the HMD itself, such as a music audio file executable by the HMD to enable the wearer to listen to music. Other types of third ("desired") audio signals are possible as well.

Figure 5:
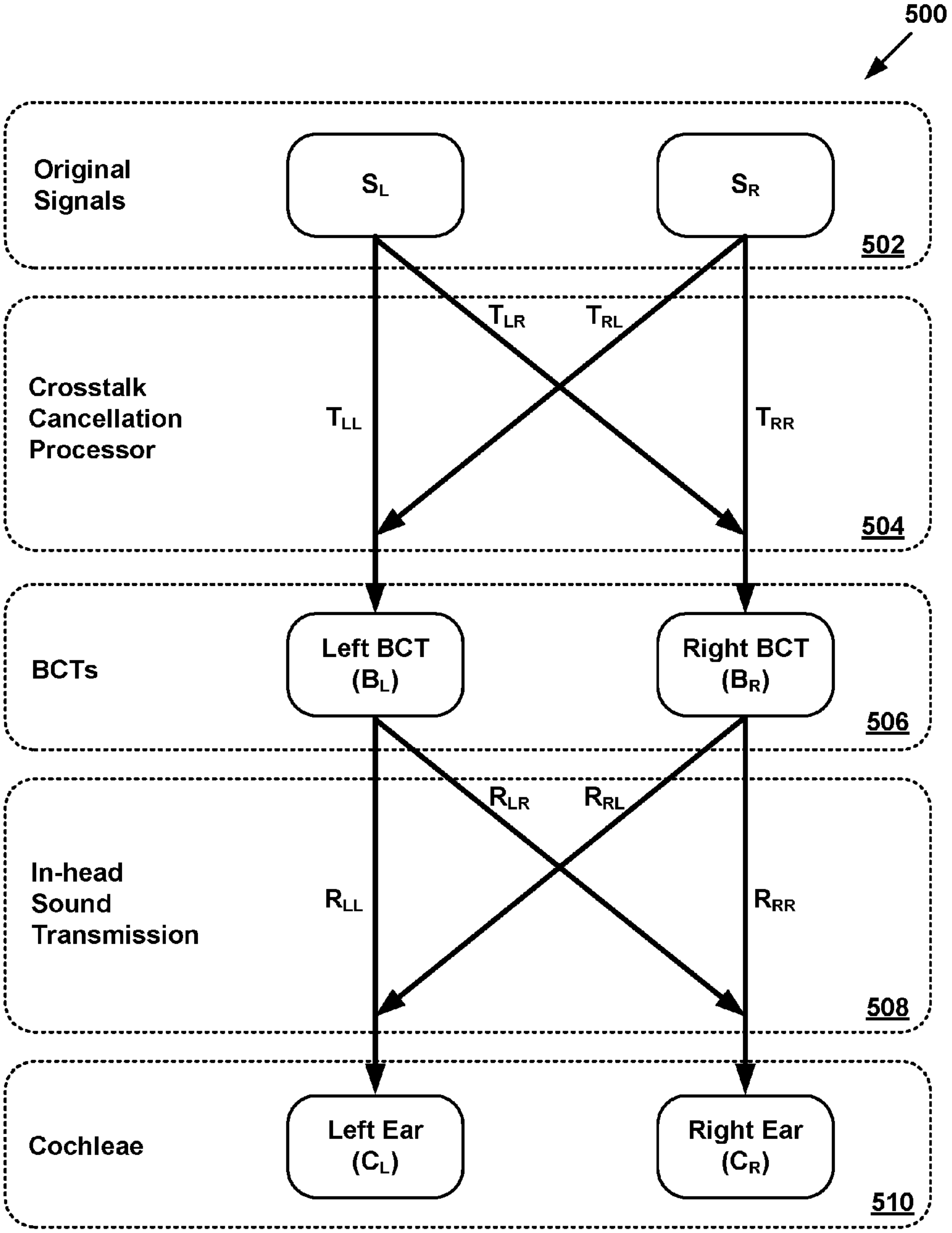
FIG. 5 is a block diagram of a system for implementing an aspect of the example method, in accordance with at least some embodiments described herein.

In some examples, the second audio signal may be determined by the noise-cancellation processor generating a signal that is anti-phased with the first audio signal. The second audio signal may then be superposed with the third audio signal and the resulting superposed signal may be subsequently multiplied by a transform. The transform (i.e., a matrix T, including the $T_{XY}$ values, as shown in FIG. 5) may be based on the one or more wearer-specific parameters, namely based on in-head response functions (i.e., a matrix R, including the $R_{XY}$ values, as shown in FIGS. 5, 6A-6D and FIG. 7) that are based on a given wearer's tissue and bone composition and structure. The in-head response functions may be further based on other aspects of the wearer's head, such as head shape, head size, and tissue parameters (e.g., type, elasticity, damping), among others. Each $T_{XY}$ value may represent a transfer function T from X audio channel to Y transducer, and each $R_{XY}$ value may represent a transfer function R from X transducer to Y cochlea. In some examples, the in-head response functions may be measured prior to the method being performed so as to calibrate the HMD for the given wearer. In other examples, the in-head response functions may be predetermined based on an average of various in-head response functions of a population of wearers.

The method described above includes a noise cancellation process implemented at one ear of the wearer, such as for single channel, monophonic audio. Therefore, in some embodiments (e.g., two channel, stereophonic audio) the same noise cancellation process may be implemented at the other ear of the wearer. In such embodiments, crosstalk signals may be present, and the same transform as noted above can be applied to each channel in order to cancel the crosstalk signals. Further, in such embodiments, the in-head response functions may be measured prior to the process being implemented so as to calibrate the HMD for the given wearer. In alternative embodiments, however, the in-head response functions may be predetermined based on an average of various in-head response functions of a large population of wearers. Other embodiments of this system are also possible Systems and devices in which example embodiments may be implemented will now be described in greater detail. In general, an example system may be implemented in or may take the form of a wearable computing device. In some examples, a wearable computing device may take the form of or include an HMD, as noted above. Henceforth, "wearable computing device" and "HMD" may be used interchangeably.

An example system may also be implemented in or take the form of other devices, such as a mobile phone, tablet computer, laptop computer, and computing appliance, each configured with sensors, cameras, and the like arranged to capture/scan a user's eye, face, or record other biometric data. Further, an example system may take the form of non-transitory computer readable medium, which has program instructions stored thereon that are executable by at a processor to provide the functionality described herein. An example system may also take the form of a device such as a wearable computer or mobile phone, or a subsystem of such a device, which includes such a non-transitory computer readable medium having such program instructions stored thereon.

An HMD may generally be any display device that is capable of being worn on the head and places a display in front of one or both eyes of the wearer. An HMD may take various forms such as a helmet or eyeglasses. As such, references to "eyeglasses" or a "glasses-style" HMD should be understood to refer to an HMD that has a glasses-like frame so that it can be worn on the head. Further, example embodiments may be implemented by or in association with an HMD with a single display or with two displays, which may be referred to as a "monocular" HMD or a "binocular" HMD, respectively.

FIG. 1A illustrates a wearable computing system according to at least some embodiments described herein. In FIG. 1A, the wearable computing system takes the form of a head-mountable device (HMD) 102 (which may also be referred to as a head-mounted display). It should be understood, however, that example systems and devices may take the form of or be implemented within or in association with other types of devices, without departing from the scope of the invention. As illustrated in FIG. 1A, the HMD 102 includes frame elements including lens-frames 104, 106 and a center frame support 108, lens elements 110, 112, and extending side-arms 114, 116. The center frame support 108 and the extending side-arms 114, 116 are configured to secure the HMD 102 to a user's face via a user's nose and ears, respectively.

Each of the frame elements 104, 106, and 108 and the extending side-arms 114, 116 may be formed of a solid structure of plastic and/or metal, or may be formed of a hollow structure of similar material so as to allow wiring and component interconnects to be internally routed through the HMD 102. Other materials may be possible as well.

One or more of each of the lens elements 110, 112 may be formed of any material that can suitably display a projected image or graphic. Each of the lens elements 110, 112 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 114, 116 may each be projections that extend away from the lens-frames 104, 106, respectively, and may be positioned behind a user's ears to secure the HMD 102 to the user. The extending side-arms 114, 116 may further secure the HMD 102 to the user by extending around a rear portion of the user's head. Additionally or alternatively, for example, the HMD 102 may connect to or be affixed within a head-mounted helmet structure. Other configurations for an HMD are also possible.

The HMD 102 may also include an on-board computing system 118, an image capture device 120, a sensor 122, and a finger-operable touchpad 124. The on-board computing system 118 is shown to be positioned on the extending side-arm 114 of the HMD 102; however, the on-board computing system 118 may be provided on other parts of the HMD 102 or may be positioned remote from the HMD 102 (e.g., the on-board computing system 118 could be wire- or wirelessly-connected to the HMD 102). The on-board computing system 118 may include a processor and memory, for example. The on-board computing system 118 may be configured to receive and analyze data from the image capture device 120 and the finger-operable touchpad 124 (and possibly from other sensory devices, user interfaces, or both) and generate images for output by the lens elements 110 and 112.

The image capture device 120 may be, for example, a camera that is configured to capture still images and/or to capture video. In the illustrated configuration, image capture device 120 is positioned on the extending side-arm 114 of the HMD 102; however, the image capture device 120 may be provided on other parts of the HMD 102. The image capture device 120 may be configured to capture images at various resolutions or at different frame rates. Many image capture devices with a small form-factor, such as the cameras used in mobile phones or webcams, for example, may be incorporated into an example of the HMD 102.

Further, although FIG. 1A illustrates one image capture device 120, more image capture device may be used, and each may be configured to capture the same view, or to capture different views. For example, the image capture device 120 may be forward facing to capture at least a portion of the real-world view perceived by the user. This forward facing image captured by the image capture device 120 may then be used to generate an augmented reality where computer generated images appear to interact with or overlay the real-world view perceived by the user.

The sensor 122 is shown on the extending side-arm 116 of the HMD 102; however, the sensor 122 may be positioned on other parts of the HMD 102. For illustrative purposes, only one sensor 122 is shown. However, in an example embodiment, the HMD 102 may include multiple sensors. For example, an HMD 102 may include sensors 102 such as one or more gyroscopes, one or more accelerometers, one or more magnetometers, one or more light sensors, one or more infrared sensors, and/or one or more microphones. Other sensing devices may be included in addition or in the alternative to the sensors that are specifically identified herein.

The finger-operable touchpad 124 is shown on the extending side-arm 114 of the HMD 102. However, the finger-operable touchpad 124 may be positioned on other parts of the HMD 102. Also, more than one finger-operable touchpad may be present on the HMD 102. The finger-operable touchpad 124 may be used by a user to input commands, and such inputs may take the form of a finger swipe along the touchpad, a finger tap on the touchpad, or the like. The finger-operable touchpad 124 may sense at least one of a pressure, position and/or a movement of one or more fingers via capacitive sensing, resistance sensing, or a surface acoustic wave process, among other possibilities. The finger-operable touchpad 124 may be capable of sensing movement of one or more fingers simultaneously, in addition to sensing movement in a direction parallel or planar to the pad surface, in a direction normal to the pad surface, or both, and may also be capable of sensing a level of pressure applied to the touchpad surface. In some embodiments, the finger-operable touchpad 124 may be formed of one or more translucent or transparent insulating layers and one or more translucent or transparent conducting layers. Edges of the finger-operable touchpad 124 may be formed to have a raised, indented, or roughened surface, so as to provide tactile feedback to a user when the user's finger reaches the edge, or other area, of the finger-operable touchpad 124. If more than one finger-operable touchpad is present, each finger-operable touchpad may be operated independently, and may provide a different function.

In a further aspect, HMD 102 may be configured to receive user input in various ways, in addition or in the alternative to user input received via finger-operable touchpad 124. For example, on-board computing system 118 may implement a speech-to-text process and utilize a syntax that maps certain spoken commands to certain actions. In addition, HMD 102 may include one or more microphones (or other types of input transducers) via which a wearer's speech may be captured. Configured as such, HMD 102 may be operable to detect spoken commands and carry out various computing functions that correspond to the spoken commands.

As another example, HMD 102 may interpret certain head-movements as user input. For example, when HMD 102 is worn, HMD 102 may use one or more gyroscopes and/or one or more accelerometers to detect head movement. The HMD 102 may then interpret certain head-movements as being user input, such as nodding, or looking up, down, left, or right. An HMD 102 could also pan or scroll through graphics in a display according to movement. Other types of actions may also be mapped to head movement.

As yet another example, HMD 102 may interpret certain gestures (e.g., by a wearer's hand or hands) as user input. For example, HMD 102 may capture hand movements by analyzing image data from image capture device 120, and initiate actions that are defined as corresponding to certain hand movements.

As a further example, HMD 102 may interpret eye movement as user input. In particular, HMD 102 may include one or more inward-facing image capture devices and/or one or more other inward-facing sensors (not shown) that may be used to track eye movements and/or determine the direction of a wearer's gaze. As such, certain eye movements may be mapped to certain actions. For example, certain actions may be defined as corresponding to movement of the eye in a certain direction, a blink, and/or a wink, among other possibilities.

HMD 102 also includes a speaker 125 for generating audio output. In one example, the speaker could be in the form of a bone conduction speaker, also referred to as a bone conduction transducer (BCT). Speaker 125 may be, for example, a vibration transducer or an electroacoustic transducer that produces sound in response to an electrical audio signal input. The frame of HMD 102 may be designed such that when a user wears HMD 102, the speaker 125 contacts the wearer. Alternatively, speaker 125 may be embedded within the frame of HMD 102 and positioned such that, when the HMD 102 is worn, speaker 125 vibrates a portion of the frame that contacts the wearer. In either case, HMD 102 may be configured to send an audio signal to speaker 125, so that vibration of the speaker may be directly or indirectly transferred to the bone structure of the wearer. When the vibrations travel through the bone structure to the bones in the middle ear of the wearer, the wearer can interpret the vibrations provided by BCT 125 as sounds.

Various types of bone-conduction transducers (BCTs) may be implemented, depending upon the particular implementation. Generally, any component that is arranged to vibrate a part of a wearer's head adjacent to the HMD 102 may be incorporated as a vibration transducer. Yet further it should be understood that an HMD 102 may include a single BCT or multiple BCTs. In addition, the location(s) of BCT(s) on the HMD may vary, depending upon the implementation. For example, a BCT may be located proximate to a wearer's temple (as shown), behind the wearer's ear, proximate to the wearer's nose, and/or at any other location where the BCT can vibrate the wearer's bone structure.

Figure 1B:
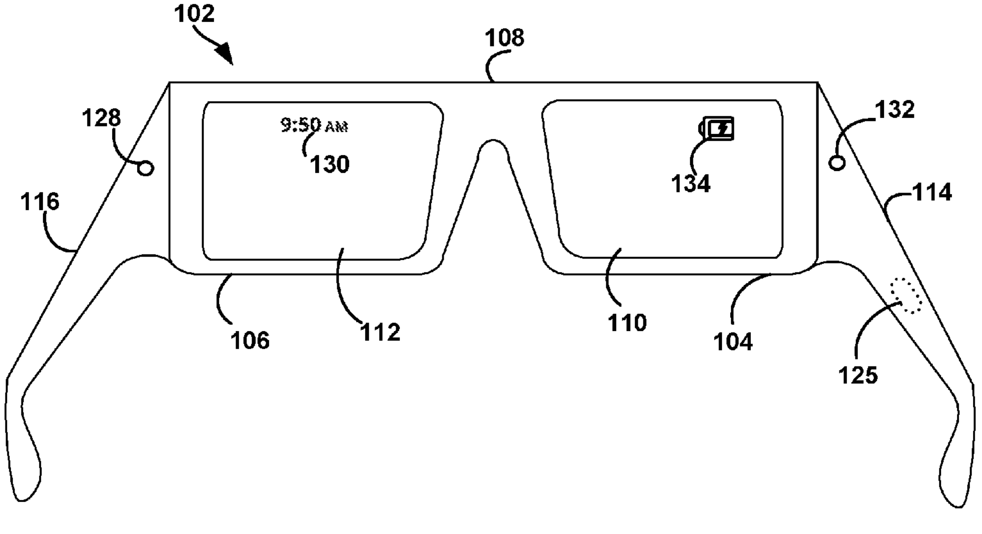
FIG. 1B illustrates an alternate view of the wearable computing system illustrated in FIG. 1A.

FIG. 1B illustrates an alternate view of the wearable computing device illustrated in FIG. 1A. As shown in FIG. 1B, the lens elements 110, 112 may act as display elements. The HMD 102 may include a first projector 128 coupled to an inside surface of the extending side-arm 116 and configured to project a display 130 onto an inside surface of the lens element 112. Additionally or alternatively, a second projector 132 may be coupled to an inside surface of the extending side-arm 114 and configured to project a display 134 onto an inside surface of the lens element 110.

The lens elements 110, 112 may act as a combiner in a light projection system and may include a coating that reflects the light projected onto them from the projectors 128, 132. In some embodiments, a reflective coating may not be used (e.g., when the projectors 128, 132 are scanning laser devices).

In alternative embodiments, other types of display elements may also be used. For example, the lens elements 110, 112 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 104, 106 for driving such a matrix display. Alternatively or additionally, a laser or LED source and scanning system could be used to draw a raster display directly onto the retina of one or more of the user's eyes. Other possibilities exist as well.

Figure 1C:
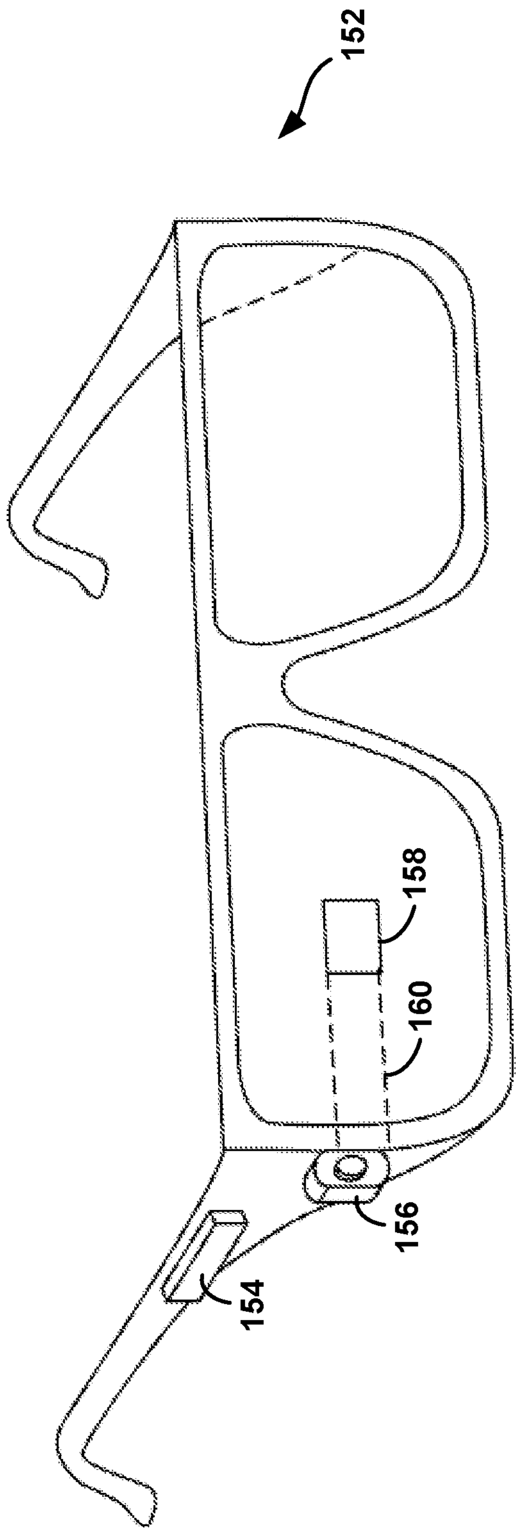
FIG. 1C illustrates another wearable computing system according to at least some embodiments described herein.

FIG. 1C illustrates another wearable computing system according to at least some embodiments described herein, which takes the form of an HMD 152. The HMD 152 may include frame elements and side-arms such as those described with respect to FIGS. 1A and 1B. The HMD 152 may additionally include an on-board computing system 154 and an image capture device 156, such as those described with respect to FIGS. 1A and 1B. The image capture device 156 is shown mounted on a frame of the HMD 152. However, the image capture device 156 may be mounted at other positions as well.

As shown in FIG. 1C, the HMD 152 may include a single display 158 which may be coupled to the device. The display 158 may be formed on one of the lens elements of the HMD 152, such as a lens element described with respect to FIGS. 1A and 1B, and may be configured to overlay computer-generated graphics in the user's view of the physical world. The display 158 is shown to be provided in a center of a lens of the HMD 152, however, the display 158 may be provided in other positions, such as for example towards either the upper or lower portions of the wearer's field of view. The display 158 is controllable via the computing system 154 that is coupled to the display 158 via an optical waveguide 160.

Figure 1D:
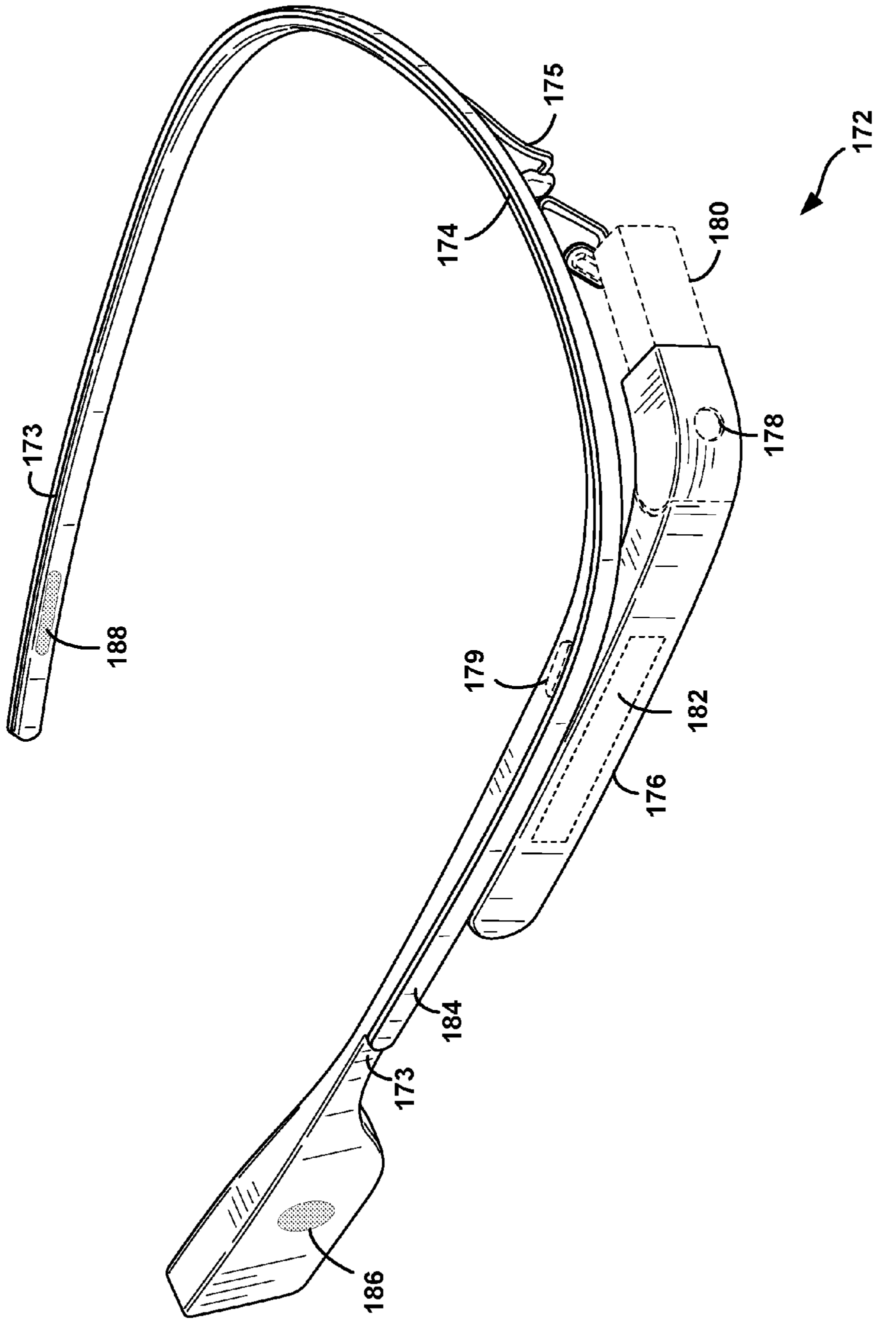
FIG. 1D illustrates another wearable computing system according to at least some embodiments described herein.

FIG. 1D illustrates another wearable computing system according to at least some embodiments described herein, which takes the form of a monocular HMD 172. The HMD 172 may include side-arms 173, a center frame support 174, and a bridge portion with nosepiece 175. In the example shown in FIG. 1D, the center frame support 174 connects the side-arms 173. The HMD 172 does not include lens-frames containing lens elements. The HMD 172 may additionally include a component housing 176, which may include an on-board computing system (not shown), an image capture device 178, a button 179 for operating the image capture device 178 (and/or usable for other purposes), and a finger-operable touch pad 182 similar to that described with respect to FIG. 1A. Component housing 176 may also include other electrical components and/or may be electrically connected to electrical components at other locations within or on the HMD. HMD 172 also includes a BCT 186. In some embodiments, HMD 172 may include at least one other BCT as well, such as BCT 188 opposite BCT 186. The BCTs may be piezoelectric BCTs (e.g., thin film piezoelectric BCTS) or other types of BCTs.

The HMD 172 may include a single display 180, which may be coupled to one of the side-arms 173 via the component housing 176. In an example embodiment, the display 180 may be a see-through display, which is made of glass and/or another transparent or translucent material, such that the wearer can see their environment through the display 180. Further, the component housing 176 may include the light sources (not shown) for the display 180 and/or optical elements (not shown) to direct light from the light sources to the display 180. As such, display 180 may include optical features that direct light that is generated by such light sources towards the wearer's eye, when HMD 172 is being worn.

In some embodiments, the HMD 172 may include one or more infrared proximity sensors or infrared trip sensors. Further, the one or more proximity sensors may be coupled to the HMD 172 at various locations, such as on the nosepiece 175 of the HMD 172, so as to accurately detect when the HMD 172 is being properly worn by a wearer. For instance, an infrared trip sensor (or other type of sensor) may be operated between nose pads of the HMD 172 and configured to detect disruptions in an infrared beam produced between the nose pads. Still further, the one or more proximity sensors may be coupled to the side-arms 173, center frame support 174, or other location(s) and configured to detect whether the HMD 172 is being worn properly. The one or more proximity sensors may also be configured to detect other positions that the HMD 172 is being worn in, such as resting on top of a head of a wearer or resting around the wearer's neck.

In a further aspect, HMD 172 may include a sliding feature 184, which may be used to adjust the length of the side-arms 173. Thus, sliding feature 184 may be used to adjust the fit of HMD 172. Further, an HMD may include other features that allow a wearer to adjust the fit of the HMD, without departing from the scope of the invention.

Figure 1E:
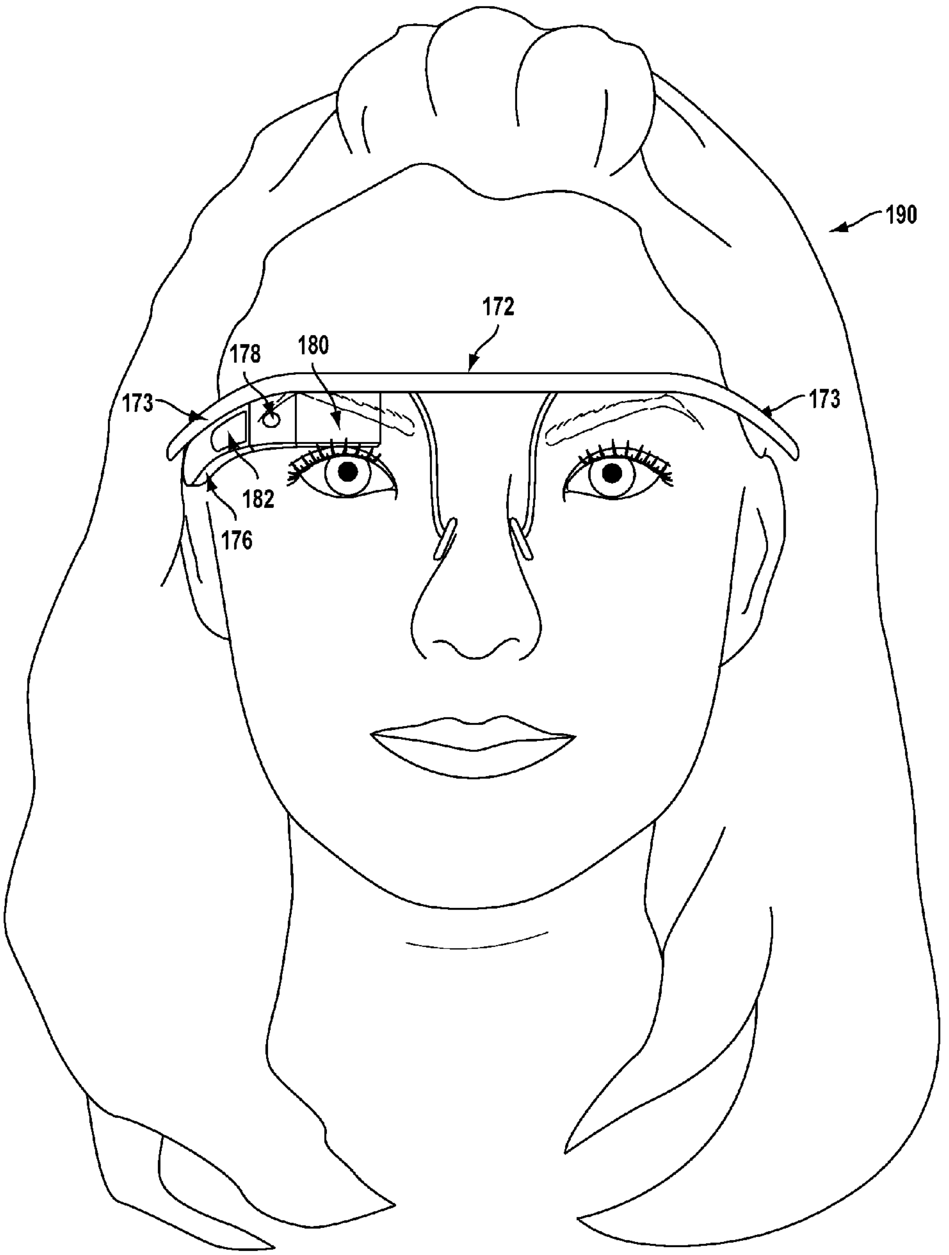
FIGS. 1E-1G are simplified illustrations of the wearable computing system shown in FIG. 1D, being worn by a wearer.
Figure 1F:
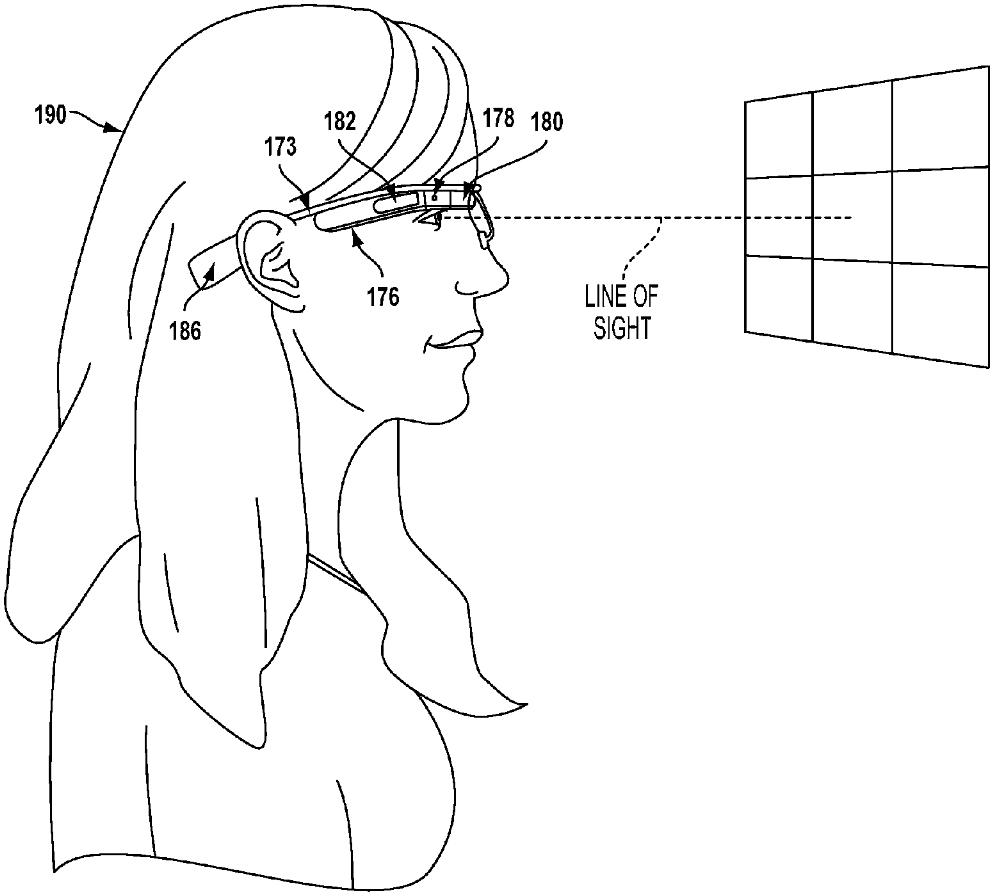
Figure 1G:
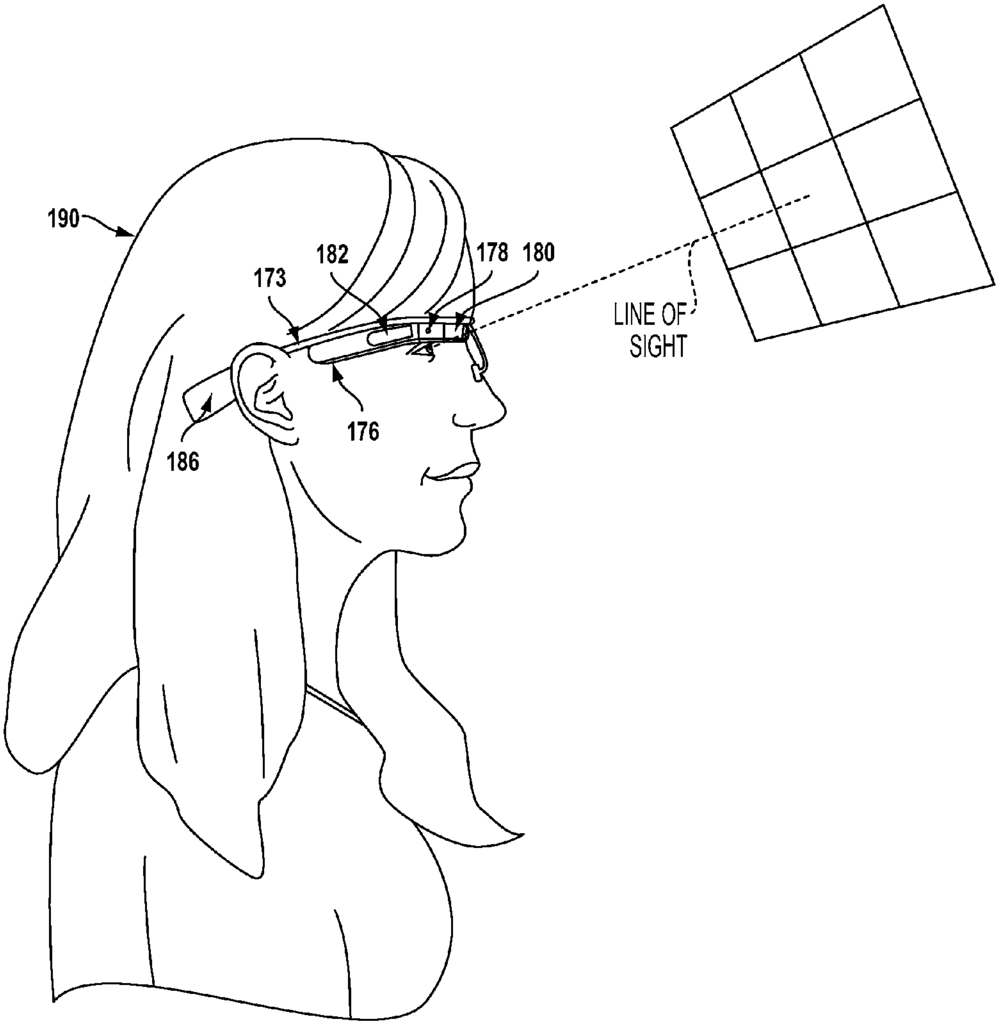

FIGS. 1E, 1F, and 1G are simplified illustrations of the HMD 172 shown in FIG. 1D, being worn by a wearer 190. As shown in FIG. 1F, when HMD 172 is worn, BCT 186 is arranged such that when HMD 172 is worn, BCT 186 is located behind the wearer's ear. As such, BCT 186 is not visible from the perspective shown in FIG. 1E. However, HMD 172 may include other BCTs such that when HMD 172 is worn, the other BCTs may contact the wearer at the wearer's right and/or left temples, at a location proximate to one or both of the wearer's ears, and/or at other locations.

In the illustrated example, the display 180 may be arranged such that when HMD 172 is worn, display 180 is positioned in front of or proximate to a user's eye when the HMD 172 is worn by a user. For example, display 180 may be positioned below the center frame support and above the center of the wearer's eye, as shown in FIG. 1E. Further, in the illustrated configuration, display 180 may be offset from the center of the wearer's eye (e.g., so that the center of display 180 is positioned to the right and above of the center of the wearer's eye, from the wearer's perspective).

Configured as shown in FIGS. 1E, 1F, and 1G, display 180 may be located in the periphery of the field of view of the wearer 190, when HMD 172 is worn. Thus, as shown by FIG. 1F, when the wearer 190 looks forward, the wearer 190 may see the display 180 with their peripheral vision. As a result, display 180 may be outside the central portion of the wearer's field of view when their eye is facing forward, as it commonly is for many day-to-day activities. Such positioning can facilitate unobstructed eye-to-eye conversations with others, as well as generally providing unobstructed viewing and perception of the world within the central portion of the wearer's field of view. Further, when the display 180 is located as shown, the wearer 190 may view the display 180 by, e.g., looking up with their eyes only (possibly without moving their head). This is illustrated as shown in FIG. 1G, where the wearer has moved their eyes to look up and align their line of sight with display 180. A wearer might also use the display by tilting their head down and aligning their eye with the display 180.

Figure 2:
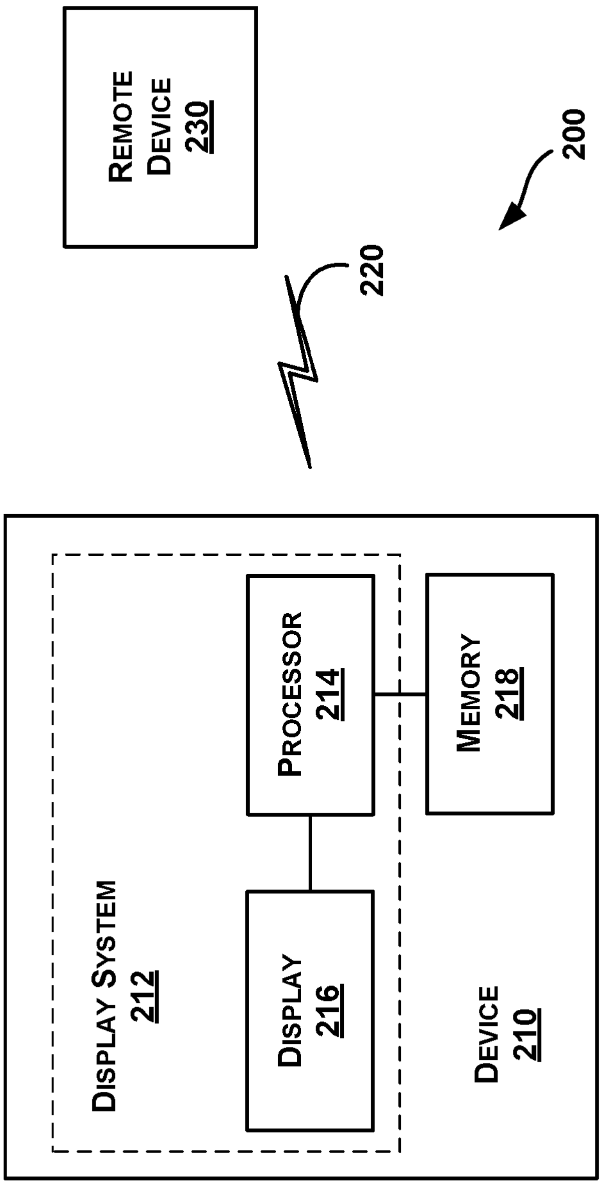
FIG. 2 illustrates a schematic drawing of a computing device according to at least some embodiments described herein.

FIG. 2 illustrates a schematic drawing of a computing device 210 according to at least some embodiments described herein. In an example embodiment, device 210 communicates using a communication link 220 (e.g., a wired or wireless connection) to a remote device 230. The device 210 may be any type of device that can receive data and display information corresponding to or associated with the data. For example, the device 210 may be a heads-up display system, such as the head-mounted devices 102, 152, or 172 described with reference to FIGS. 1A to 1G.

Thus, the device 210 may include a display system 212 comprising a processor 214 and a display 216. The display 210 may be, for example, an optical see-through display, an optical see-around display, or a video see-through display. The processor 214 may receive data from the remote device 230, and configure the data for display on the display 216. The processor 214 may be any type of processor, such as a micro-processor or a digital signal processor, for example. The processor 214 may also include other processors, such as a crosstalk cancellation processor (not shown), which may be implemented in accordance with at least one example embodiment described herein.

The device 210 may further include on-board data storage, such as memory 218 coupled to the processor 214. The memory 218 may store software that can be accessed and executed by the processor 214, for example.

The remote device 230 may be any type of computing device or transmitter including a laptop computer, a mobile telephone, or tablet computing device, etc., that is configured to transmit data to the device 210. The remote device 230 and the device 210 may contain hardware to enable the communication link 220, such as processors, transmitters, receivers, antennas, etc.

Further, remote device 230 may take the form of or be implemented in a computing system that is in communication with and configured to perform functions on behalf of client device, such as computing device 210. Such a remote device 230 may receive data from another computing device 210 (e.g., an HMD 102, 152, or 172 or a mobile phone), perform certain processing functions on behalf of the device 210, and then send the resulting data back to device 210. This functionality may be referred to as "cloud" computing.

In FIG. 2, the communication link 220 is illustrated as a wireless connection; however, wired connections may also be used. For example, the communication link 220 may be a wired serial bus such as a universal serial bus or a parallel bus. A wired connection may be a proprietary connection as well. The communication link 220 may also be a wireless connection using, e.g., short range wireless radio technology, communication protocols described in IEEE 802.11 (including any IEEE 802.11 revisions), Cellular technology (such as GSM, CDMA, UMTS, EV-DO, WiMAX, or LTE), or personal area network technology, among other possibilities. The remote device 230 may be accessible via the Internet and may include a computing cluster associated with a particular web service (e.g., social-networking, photo sharing, address book, etc.).

Figure 3:
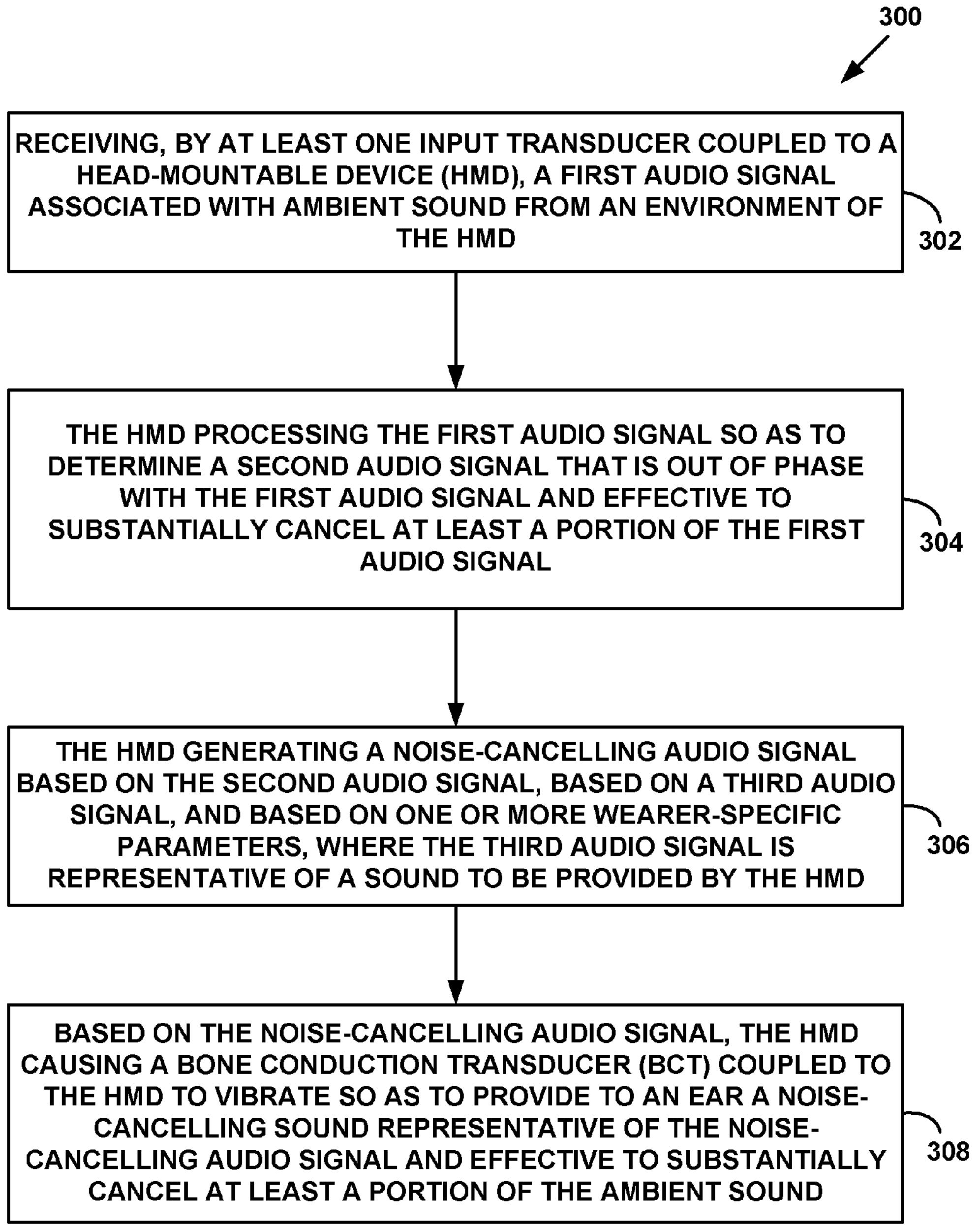
FIG. 3 is a flow chart of an example method according to at least some embodiments described herein.

FIG. 3 is a flow chart of an example method 300, according to at least some embodiments described herein. Method 300 may include one or more operations, functions, or actions as illustrated by one or more of blocks 302-308. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 300 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include a non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable medium may also be any other volatile or non-volatile storage systems. The computer readable medium may be considered a computer readable storage medium, for example, or a tangible storage device.

In addition, for the method 300 and other processes disclosed herein, each block in FIG. 3 may represent circuitry that is wired to perform the specific logical functions in the process.

For the sake of example, the method 300 will be described as implemented by an example head-mountable device (HMD), such as the HMDs illustrated in FIGS. 1A-1G. It should be understood, however, that other computing devices, such as wearable computing devices (e.g., watches), or combinations of computing devices maybe configured to implement one or more steps of the method 300.

At block 302, the method 300 includes an HMD receiving, by at least one input transducer coupled to the HMD, a first audio signal associated with ambient sound from an environment of the HMD. The at least one input transducer may include one or more microphones coupled to the HMD.

At block 304, the method 300 includes the HMD processing the first audio signal so as to determine a second audio signal that is out of phase with the first audio signal and effective to substantially cancel at least a portion of the first audio signal. In some examples, the processing may be performed by a noise cancellation processor and/or other processor(s) of the HMD.

In some examples, the second audio signal may be in anti-phase (i.e., about or exactly 180 degrees out of phase) with the first audio signal. In other examples, the second audio signal may be more or less than 180 degrees out of phase with the first audio signal.

At block 306, the method 300 includes the HMD generating a noise-cancelling audio signal based on the second audio signal, based on a third audio signal, and based on one or more wearer-specific parameters (e.g., unique properties of a given wearer's head and/or torso), where the third audio signal is representative of a sound to be provided by the HMD. The wearer-specific parameters may include wearer-specific mechanical-acoustical parameters based on a bone thickness of a skull of the wearer, a bone shape of the wearer, a tissue thickness and tissue distribution of a head of the wearer, a threshold sensitivity and dynamic range of the given wearer's auditory system as decided by the wearer's specific anatomic and physiological features (e.g., inner ear, auditory nervous system, etc.), and/or other parameters of the wearer's head and/or torso described herein or not described herein.

In some examples, the noise-cancelling audio signal may include a superposition of the second audio signal and the third audio signal. The third audio signal may also be referred to herein as a "desired" audio signal, because the third audio signal may take the form of a voice communication signal, a music signal, or other audio signal that is intended to be perceived by the wearer. As such, the sound to be provided by the HMD may be a voice communication sound, music, or other sound based on the third audio signal.

In some examples, the desired audio signal may be originated at the HMD (e.g., an mp3). In other examples, the desired audio signal may be received by the HMD from another computing device (e.g., voice communication, a voicemail, etc.).

The generation of the noise-cancelling audio signal may involve the HMD (e.g., one or more processors of the HMD) multiplying the superposed second and third audio signal by a transform. The resulting noise-cancelling audio signal may have approximately the same amplitude (or exactly the same amplitude) as the first audio signal. Derivation/measurement of the transform, $\vec{T}$, which can be based on the in-head response functions discussed above, is described herein with respect to FIG. 5, FIGS. 6A-6D, and FIG. 7.

At block 308, the method 300 includes, based on the noise-cancelling audio signal, the wearable computing device causing a bone conduction transducer (BCT) coupled to the wearable computing device to vibrate so as to provide to an ear a noise-cancelling sound representative of the noise-cancelling audio signal and effective to substantially cancel at least a portion of the ambient sound. The BCT may be located adjacent to one side of the wearer's head on the same side as the ear of the wearer (e.g., located proximate to the ear of the wearer).

Figure 4A:
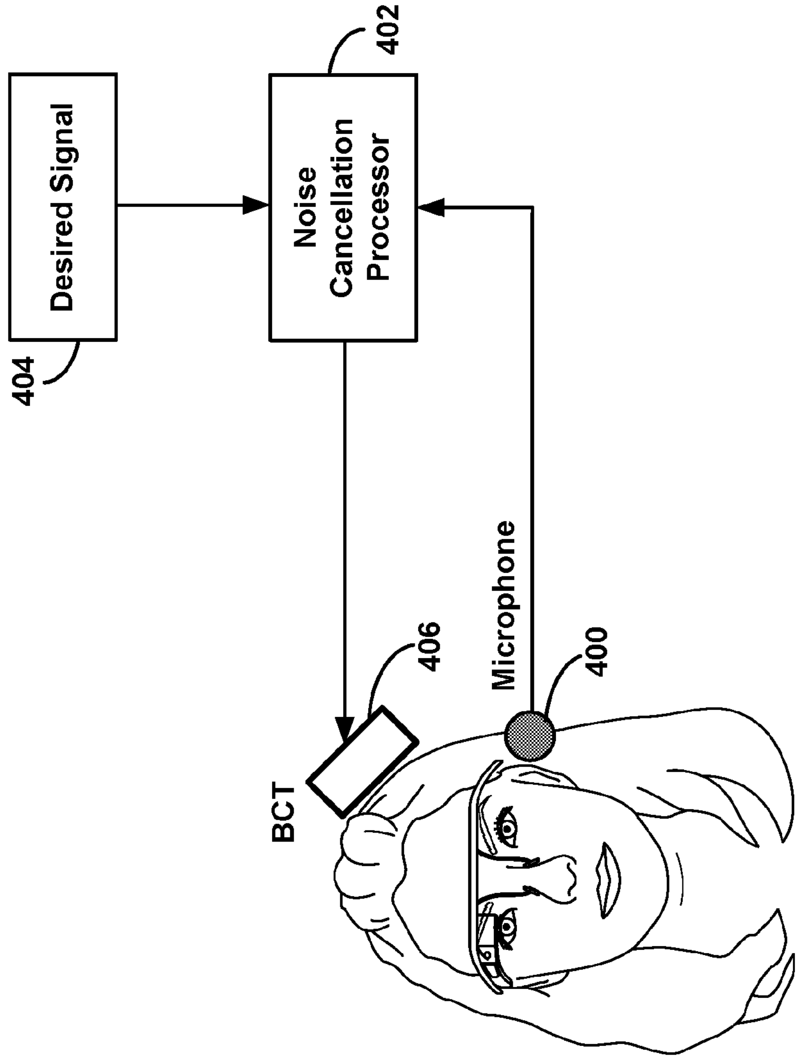
FIGS. 4A and 4B are block diagrams of two conceptual implementations of the example method, in accordance with at least some embodiments described herein.
Figure 4B:
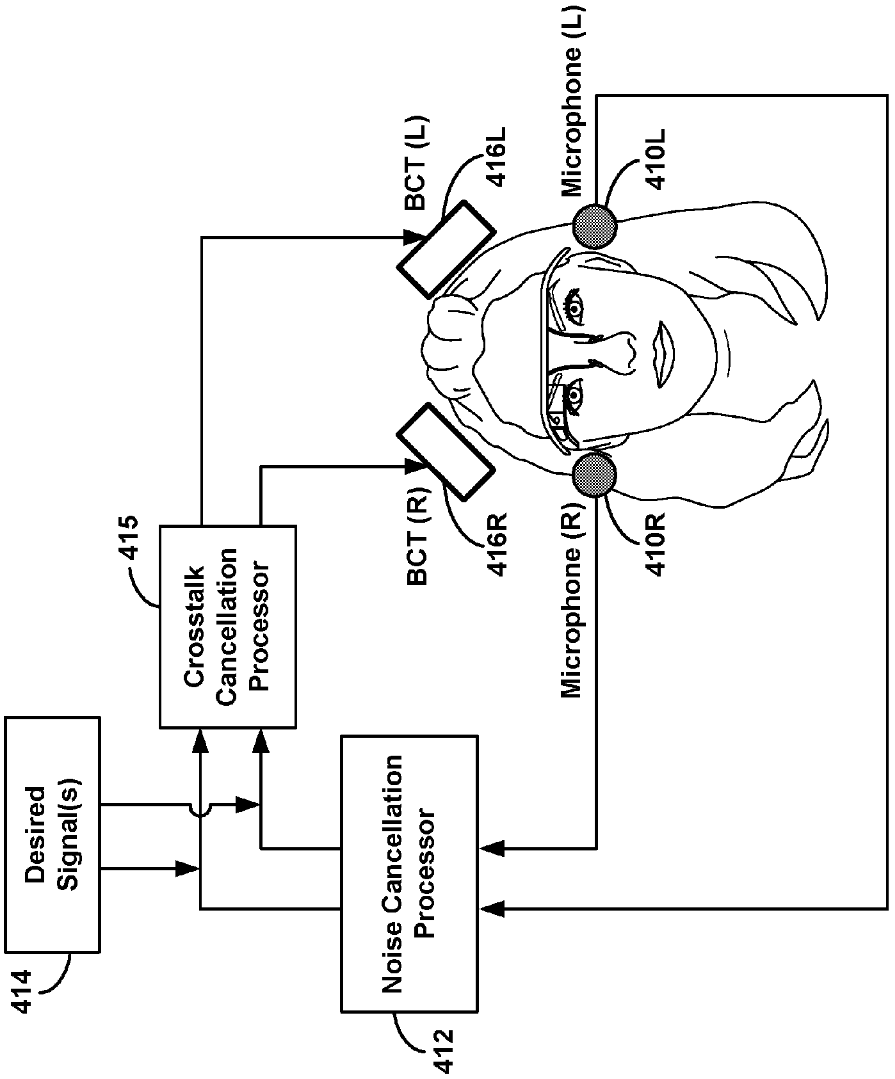

FIG. 4A is a block diagram of a conceptual implementation of the method 300, in accordance with at least some embodiments described herein. In particular, the implementation shown in FIG. 4A is a single channel implementation, as opposed to a two channel (e.g., stereo, binaural, etc.) implementation shown in FIG. 4B. The implementation shown in FIG. 4A can be implemented on either side of a wearer's head, and the illustration is for example purposes as other implementations or configurations of components in FIG. 4A are possible as well.

As shown, an input transducer coupled to the HMD such as a microphone 400 may receive a first audio signal such as an ambient noise signal. A noise cancellation processor 402 coupled to the HMD may then receive the ambient noise signal and responsively determine a second audio signal based on the ambient noise signal, where the second audio signal is in anti-phase with the first audio signal. The HMD (e.g., the noise cancellation processor 402 or other component of the HMD) may then receive a desired audio signal 404 and superpose the second audio signal with a desired audio signal 404.

The noise cancellation processor 402 may then apply a transform to the superposed audio signal so as to determine a noise-cancelling audio signal. In some examples, the HMD may include a separate processor (not shown) or other component that may apply the transform. Other examples are also possible. In some examples, the transform may be applied before the superposing of the second and third audio signals. In other examples, the transform may not be applied.

The resulting noise-cancelling audio signal may then be converted to a noise-cancelling sound by a BCT 406 coupled to the HMD and transmitted to an ear of the wearer of the HMD on the same side as where the first audio signal was received. It should be understood that other variations of the single channel implementation are also possible. Although FIG. 4A illustrates the BCT 406 separate from the HMD eyeglasses, this is for illustration purposes only, and the BCT 406 may be included within a frame of the HMD eyeglasses in other examples. In addition, the microphone 400 may also be included within the HMD eyeglasses as well.

For a two channel implementation, the method 300 can be performed with respect to both sides of the wearer's head (e.g., stereo audio with noise cancellation). However, due to transmission of bone-conducted signals through the wearer's head, when a bone-conducted signal is intended to be heard by the wearer's right ear only, part of that signal may also be heard by the wearer's left ear. Likewise, when a bone-conducted signal is intended to be heard by the wearer's left ear only, part of that signal may also be heard by the wearer's right ear. The parts of the intended signals that are heard by ears contralateral to the intended ears are known as crosstalk signals. As noted above, crosstalk sound may result from the transmission of the noise-cancelling sound to respective ears of the wearer, and therefore the HMD may include a crosstalk cancellation processor for generating signals that may substantially cancel crosstalk signals.

As noted above, FIG. 4B is a block diagram of a two channel implementation of the method 300, in accordance with at least some embodiments described herein. In some examples of this implementation, an input transducer such as a left microphone 410L may receive a first audio signal such as an ambient noise signal associated with an ambient sound from an environment of the HMD. A noise cancellation processor 412 may then receive the ambient noise signal and responsively determine a second audio signal that is in anti-phase with the ambient noise signal. The HMD (e.g., the noise cancellation processor 412 or another component of the HMD) may then superpose the second audio signal with a third audio signal, such as a desired stereo audio signal 414. In some examples the superposing may be performed by a crosstalk cancellation processor 415.

The HMD may also receive, via another input transducer such as a right microphone 410R, a fourth audio signal such as another ambient noise signal associated with the same ambient sound or another ambient sound from the environment of the HMD. A noise cancellation processor 412 may then receive the other ambient noise signal and responsively determine a fifth audio signal that is in anti-phase with the other ambient noise signal. The HMD may then superpose the fifth audio signal with a sixth audio signal, such as another desired stereo audio signal 414. In some examples the superposing may be performed by a crosstalk cancellation processor 415.

The crosstalk cancellation processor 415 (or other component of the HMD) may then apply a transform to each of the superposed audio signals so as to determine respective noise-and-crosstalk-cancelling audio signals. In some examples, the crosstalk cancellation processor 415 may be a single processor configured to implement any or all crosstalk and noise cancellation functions. In other examples, the crosstalk cancellation processor 415 may include separate processors for crosstalk cancellation functions, for noise cancellation functions, and/or for other possible functions.

Typically, the superposed audio signals for each of the two audio channels may have crosstalk effects on the signal of the opposite audio channel, and thus the noise-and-crosstalk-cancelling audio signals resulting from the application of the transform may be each effective to substantially cancel the crosstalk effects from the opposite audio channel. To facilitate this, each of the noise-and-crosstalk-cancelling audio signals may be out of phase with the crosstalk signals from the opposite audio channels.

The noise-and-crosstalk-cancelling audio signals may then be converted to noise-and-crosstalk-cancelling sounds by a left BCT 416L and a right BCT 416R coupled to the HMD and transmitted to a left ear of the wearer and a right ear, respectively. In particular, a given noise-and-crosstalk-cancelling sound may be transmitted to the left ear via the left BCT 416L that is on the same side as where the first audio signal was received (e.g., the left microphone 410L) and may be effective to substantially cancel crosstalk sound from the right BCT 416R. Likewise, the other noise-and-crosstalk-cancelling sound may be transmitted to the right ear via the BCT 416R that is on the same side as where the fourth audio signal was received (e.g., the right microphone 410R) and may be effective to substantially cancel crosstalk sound from the left BCT 416L. It should be understood that other variations of the two channel implementation are also possible.

The BCTs may contact the wearer at the back of their respective ears (e.g., mastoid) or at another location such as a temple of the wearer or other location on the same side of the wearer's head as their respective ears. Other locations are possible as well, such as locations proximate to the wearer's condyles or temples. A given BCT may thus vibrate the wearer's skull and provide the desired sound to the inner ear of one ear and provide the crosstalk sound to the inner ear of the other ear.

In some examples, the BCTs may vibrate simultaneously. In other examples, the BCTs may vibrate at different times, with one BCT vibrating prior to the other BCT.

While in some examples, the crosstalk sound may be entirely cancelled by the noise-and-crosstalk-cancelling sound, the crosstalk sound may not be entirely cancelled in other examples. Rather, the crosstalk sound may be at least partially cancelled by the noise-and-crosstalk-cancelling sound. Other examples are also possible.

In some examples, the transform applied for the single channel implementation may be the same as the transform applied for the two channel implementation. In other examples, however, the transforms may be different.

In some examples the method 300 and related processes described herein may be implemented using two BCTs and/or two input transducers (e.g., microphones). However, it should be understood that in other examples, more than two BCTs may be used and/or more than two input transducers may be used, in which case ambient noise cancellation may be the same for each channel, yet crosstalk cancellation may involve an expansion of the transfer functions and matrices discussed herein.

FIG. 5 is a block diagram of a system 500 for implementing the crosstalk cancellation process in accordance with at least some embodiments described herein. The system 500 may include original signals 502, $S_L$ and $S_R$, which represent stereophonic audio signals that are intended to be heard by a left ear and a right ear of a wearer of an HMD, respectively. For example, $S_L$ and $S_R$ may take the form of the superposed audio signals described above.

In some examples, the original signals 502 may be processed by a crosstalk cancellation processor 504 of the HMD to preemptively account for the crosstalk effect caused by the wearer's head. In other words, the crosstalk cancellation processor 504 may modify the original signals 502 to each include a component that is effective to substantially cancel any crosstalk signal from the opposite ear. Left and right BCTs 506 may then produce stereo sound based on the modified signals. For instance, as shown, the crosstalk cancellation processor 504 may apply response function $T_{LR}$ to original signal $S_L$ in order to generate a crosstalk-cancelling signal effective to cause the right BCT to produce a corresponding crosstalk-cancelling sound simultaneous to the left BCT producing an original sound based on original signal $S_L$.

Likewise, as shown, the crosstalk cancellation processor 504 may apply response function $T_{RL}$ to original signal $S_R$ in order to generate a crosstalk-cancelling signal effective to cause the left BCT to produce a corresponding crosstalk-cancelling sound simultaneous to the right BCT producing an original sound based on original signal $S_R$.

In other examples, prior to the HMD processing the original signals 502 with the crosstalk cancellation processor 504, the HMD may apply a head-related transfer function (HRTF) to the original signals 502, where the HRTF is associated with the wearer and based on the wearer-specific parameters. In some examples, the HRTF may comprise two transfer functions, one for each side of the wearer (e.g., left and right sides), and each representative of the diffraction of an incoming sound waveform by a torso and a head of a particular wearer. The HRTF may be measured so as to be unique for the particular wearer of the HMD, or the HRTF may be predetermined based on an average of various measured HRTFs of a population of wearers. Implementation of the HRTF may be effective to create a more realistic sound image.

In some examples, the original signals 502 and crosstalk-cancelling signals may then be transmitted to the wearer of the HMD via BCTs 506, namely a left BCT and a right BCT with corresponding responses $B_L$ and $B_R$, respectively. The BCTs' 506 responses may be represented by Equation 1.

$$\begin{bmatrix} B_L \\ B_R \end{bmatrix} = \begin{bmatrix} T_{LL} & T_{RL} \\ T_{LR} & T_{RR} \end{bmatrix} \cdot \begin{bmatrix} S_L \\ S_R \end{bmatrix} \quad \text{Equation (1)}$$

As an example, in a monophonic scenario, such as when $S_R$ is equal to zero, the response of the left BCT and the response of the right BCT may be represented by Equation 2 and Equation 3, respectively.

$$B_L = T_{LL} * S_L \quad \text{Equation (2)}$$

$$B_R = T_{LR} * S_L \quad \text{Equation (3)}$$

Likewise, in another monophonic scenario when $S_L$ is equal to zero, the response of the left BCT and the response of the right BCT may be represented by Equation 4 and Equation 5, respectively.

$$B_L = T_{RL} * S_R \quad \text{Equation (4)}$$

$$B_R = T_{RR} * S_R \quad \text{Equation (5)}$$

On the other hand, in a stereophonic scenario, the response of the left BCT and the response of the right BCT may be represented by Equation 6 and Equation 7, respectively.

$$B_L = T_{LL} * S_L + T_{RL} * S_R \quad \text{Equation (6)}$$

$$B_R = T_{LR} * S_L + T_{RR} * S_R \quad \text{Equation (7)}$$

After the BCTs 506 vibrate to produce stereo audio sound, the stereo audio sound travels through an in-head transmission path 508 before being received at the wearer's left and right cochleae 510. In general, the responses at a wearer's cochleae 510 may be represented by Equation 8.

$$\begin{bmatrix} C_L \\ C_R \end{bmatrix} = \begin{bmatrix} R_{LL} & R_{RL} \\ R_{LR} & R_{RR} \end{bmatrix} \cdot \begin{bmatrix} B_L \\ B_R \end{bmatrix} \quad \text{Equation (8)}$$

As shown in Equation 8, the signals received at the wearer's left and right cochlea, $C_L$ and $C_R$, are determined by multiplying the BCT signals, $B_L$ and $B_R$, by an in-head response matrix. For the in-head response matrix, $R_{LL}$ and $R_{RR}$ represent the response of the direct paths from the left BCT to the left cochlea and from the right BCT to the right cochlea, respectively. Further, $R_{LR}$ and $R_{RL}$ represent the response of the crosstalk paths from the left BCT to the right cochlea and from the right BCT to the left cochlea, respectively.

As such, by the HMD's implementation of the crosstalk cancellation processor 504, the responses at the wearer's cochleae 510 may be represented by Equation 9, which is a combination of Equation 1 and Equation 8.

$$\begin{bmatrix} C_L \\ C_R \end{bmatrix} = \begin{bmatrix} R_{LL} & R_{RL} \\ R_{LR} & R_{RR} \end{bmatrix} \cdot \begin{bmatrix} T_{LL} & T_{RL} \\ T_{LR} & T_{RR} \end{bmatrix} \cdot \begin{bmatrix} S_L \\ S_R \end{bmatrix} \quad \text{Equation (9)}$$

Further, in order to have the original signals 502 equal the stereo audio signals that reach the wearer's cochleae 510, thereby providing the wearer with a stereo audio experience with substantially cancelled crosstalk from the in-head responses, $R_{LR}$ and $R_{RL}$, the transform $\vec{T}$ can equal the inverse of the in-head response, as shown in Equation 10.

$$\vec{T} = \vec{R}^{-1} = \left(\frac{1}{R_{LL}R_{RR} - R_{RL}R_{LR}}\right) \cdot \begin{bmatrix} R_{RR} & -R_{RL} \\ -R_{LR} & R_{LL} \end{bmatrix} \quad \text{Equation (10)}$$

It should be understood that for embodiments where the system 400 is implemented with more than two BCTs, the matrices noted above may be larger in accordance with the amount of BCTs present. However, the same relationships between the variables may still apply.

FIGS. 6A-6D illustrate various configurations of a simplified system for measuring a transform, in accordance with at least some embodiments described herein. In particular, each of FIGS. 6A-6D illustrate a respective simplified system for measuring a given in-head response ($R_{XY}$) of the transform $\vec{T}$ described above (e.g., R from X transducer to Y cochlea). Further, each respective simplified system includes a wearer wearing an HMD such as the HMDs or other wearable computing devices described herein.

Figure 6A:
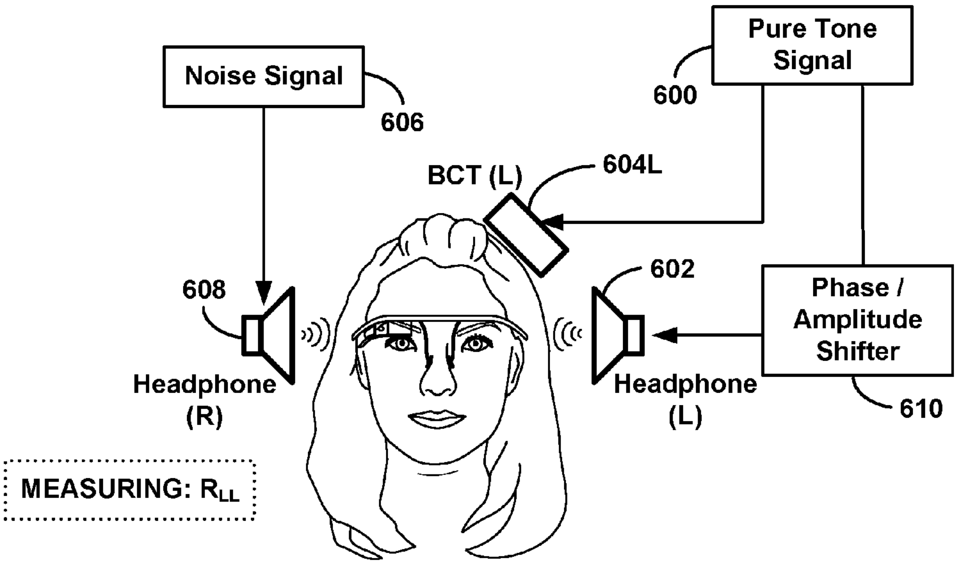
FIGS. 6A-6D illustrate various configurations of a simplified system for measuring a transform, in accordance with at least some embodiments described herein.

FIG. 6A illustrates a simplified system for measuring in-head response $R_{LL}$. To measure $R_{LL}$, the HMD may transmit a first pure tone signal 600 to a left ear of the wearer (e.g., an outer and middle ear of the left ear) via a left output transducer 602 (e.g., a headphone or earphone) that is coupled to the HMD. The transmission may be effective to provide an air-conducted pure tone sound to the left ear of the wearer. The amplitude and phase of the first pure tone signal 600 may be predetermined or determined by the wearer of the HMD. Further, in other examples, similar or different first and/or second pure tone signals may be used for measuring other $R_{XY}$ values. For instance, different frequencies and frequency bands of the first and/or second pure tone signals may be used for each $R_{XY}$ value.

The HMD may also transmit a second pure tone signal 600 to the left ear of the wearer. In some examples, the second pure tone signal 600 may have the same initial parameters as the first pure tone signal 600. In other examples, the second pure tone signal 600 may have different initial parameters than the first pure tone signal 600. The transmission of the second pure tone signal 600 may be effective to cause a left BCT 604L to vibrate so as to provide a portion of a bone-conducted pure tone sound to the left ear of the wearer (e.g., the inner ear of the left ear) and another portion of the bone-conducted pure tone sound (e.g., crosstalk sound) to the right ear of the wearer (e.g., the inner ear of the right ear). Further, it should be understood that similar or different second pure tone signals may be used for measuring other $R_{XY}$ values, including signals at varying frequencies and frequency bands.

Furthermore, substantially simultaneous to the HMD transmitting the first pure tone signal 600, the HMD may transmit a noise signal 606 to the right ear of the wearer (e.g., an outer and middle ear of the right ear) via a right output transducer 608. The noise signal 606 may be effective to provide a noise to the right ear of the wearer and substantially mask the other portion of the bone-conducted pure tone sound (due to the left ear being measured) so that the wearer can hear both the air-conducted pure tone sound and the portion of the bone-conducted pure tone sound at the left ear of the wearer without distraction by sound at the right ear of the wearer. In some examples, including each example shown in FIGS. 6A-6D, the HMD may continuously transmit the noise signal 606. For instance, the noise signal 606 may take the form of an mp3 or other sound clip repeatedly played by the HMD. In other examples, the HMD may begin transmitting the noise signal 606 within a given time interval before the HMD transmits the first pure tone signal 600, and then the HMD may stop transmitting the noise signal 606 within a given time interval after the HMD stops transmitting the first pure tone signal 600. In still other examples, the amplitude of the noise signal may be predetermined and may be the same (or different) for each in-head response measurement. Other examples are also possible.

Moreover, while the first and second pure tone signals 600 and the noise signal 606 are being transmitted to the wearer of the HMD, the wearer may adjust the phase and/or amplitude of the first pure tone signal 600 being transmitted by the left output transducer 602 via a phase/amplitude shifter 610 coupled to the HMD until no sound (or minimal sound) is perceived at the left ear of the wearer. For instance, the wearer may adjust the phase and/or amplitude of the first pure tone signal 600 until the air-conducted pure tone sound at least substantially masks the portion of the bone-conducted pure tone sound at the left ear of the wearer. Because each wearer's wearer-specific parameters are unique, the adjustments made to the phase and/or amplitude of the first pure tone signal 600 may be different for each wearer. In some scenarios, based on the adjustments, the air-conducted pure tone sound may be almost 180 degrees out of phase with the bone-conducted pure tone sound, yet other scenarios are also possible. In some examples, the adjustments may be made by the wearer via the finger-operable touch pad 182, as shown in FIG. 1D, or another input device. Based on the adjustments to the phase and amplitude of the first pure tone signal 600, the HMD may determine $R_{LL}$.

Each $R_{XY}$ value may include a respective amplitude response and a respective phase response. In some examples, the HMD may determine the amplitude response directly from the phase/amplitude shifter 610, and the HMD may determine the phase response by adding 180 degrees to the adjusted value of the phase of the first pure tone signal 600 that is outputted by the phase/amplitude shifter 610 received by the left (or right, in some examples) output transducer. In other examples, the HMD may include a microphone coupled proximate to the left ear for measuring $R_{LL}$ and $R_{RL}$ (or proximate to the right ear for measuring $R_{RR}$ and $R_{LR}$). Other locations of the microphone are possible. Other examples are possible as well.

Figure 6B:
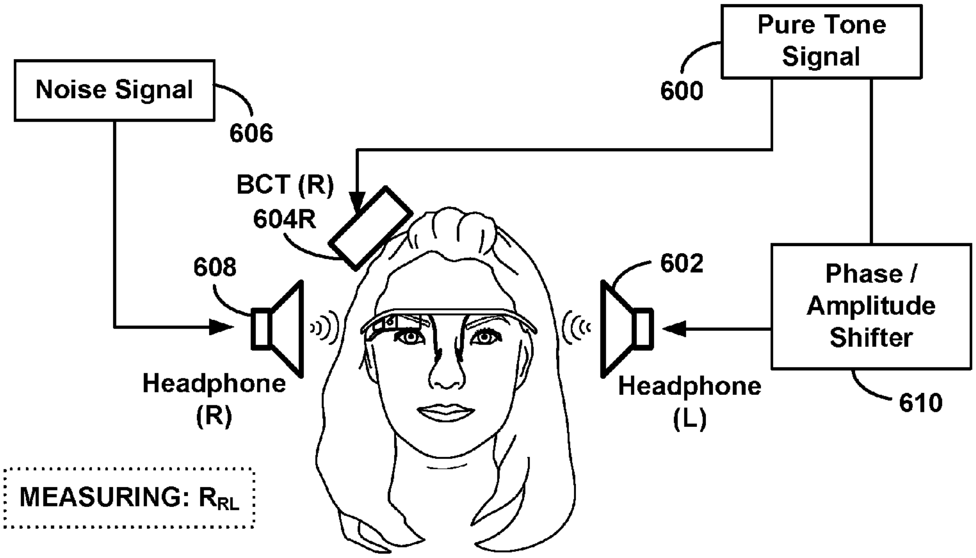

FIG. 6B illustrates a simplified system for measuring in-head response $R_{RL}$. To measure $R_{RL}$, the HMD may transmit a first pure tone signal 600 to a left ear of the wearer via the left output transducer 602 that is coupled to the HMD. The transmitting may be effective to provide an air-conducted pure tone sound to the left ear of the wearer.

The HMD may also transmit a second pure tone signal 600 to the left ear of the wearer. The transmission of the second pure tone signal 600 may be effective to cause a right BCT 604R to vibrate so as to provide a portion of a bone-conducted pure tone sound to the right ear of the wearer and another portion of the bone-conducted pure tone sound (e.g., crosstalk sound) to the left ear of the wearer.

Furthermore, substantially simultaneous to the HMD transmitting the first pure tone signal 600, the HMD may transmit a noise signal 606 to the right ear of the wearer via a right output transducer 608. The noise signal 606 may be effective to provide a noise to the right ear of the wearer and substantially mask the portion of the bone-conducted pure tone sound at the right ear (due to the left ear being measured) so that the wearer can hear both the air-conducted pure tone sound and the other portion of the bone-conducted pure tone sound at the left ear of the wearer without distraction by sound at the right ear of the wearer.

Moreover, while the first and second pure tone signals 600 and the noise signal 606 are being transmitted to the wearer of the HMD, the wearer may adjust the phase and/or amplitude of the first pure tone signal 600 being transmitted by the left output transducer 602 via a phase/amplitude shifter 610 coupled to the HMD until no sound (or minimal sound) is perceived at the left ear of the wearer. For instance, the wearer may adjust the phase and/or amplitude of the first pure tone signal 600 until the air-conducted pure tone sound at least substantially masks the other portion of the bone-conducted pure tone sound at the left ear of the wearer. Based on the adjustments to the phase and amplitude of the first pure tone signal 600, the HMD may determine $R_{RL}$ (e.g., crosstalk).

Figure 6C:
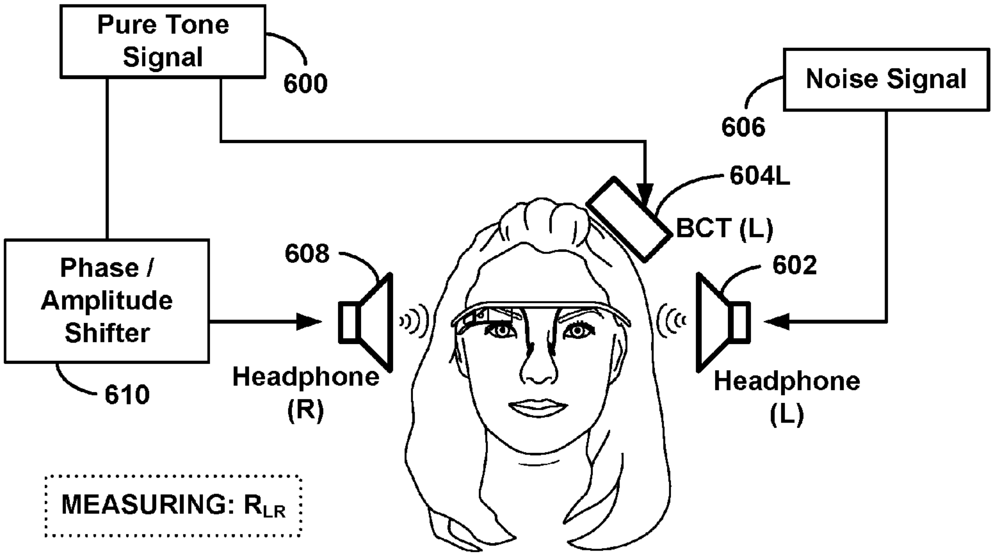

FIG. 6C illustrates a simplified system for measuring in-head response $R_{LR}$. To measure $R_{LR}$, the HMD may transmit a first pure tone signal 600 to a right ear of the wearer via the right output transducer 608 that is coupled to the HMD. The transmitting may be effective to provide an air-conducted pure tone sound to the right ear of the wearer.

The HMD may also transmit a second pure tone signal 600 to the left ear of the wearer. The transmission of the second pure tone signal 600 may be effective to cause a left BCT 604L to vibrate so as to provide a portion of a bone-conducted pure tone sound to the left ear of the wearer and another portion of the bone-conducted pure tone sound (e.g., crosstalk sound) to the right ear of the wearer.

Furthermore, substantially simultaneous to the HMD transmitting the first pure tone signal 600, the HMD may transmit a noise signal 606 to the left ear of the wearer via a left output transducer 602. The noise signal 606 may be effective to provide a noise to the left ear of the wearer and substantially mask the portion of the bone-conducted pure tone sound at the left ear (due to the right ear being measured) so that the wearer can hear both the air-conducted pure tone sound and the other portion of the bone-conducted pure tone sound at the right ear of the wearer without distraction by sound at the left ear of the wearer.

Moreover, while the first and second pure tone signals 600 and the noise signal 606 are being transmitted to the wearer of the HMD, the wearer may adjust the phase and/or amplitude of the first pure tone signal 600 being transmitted by the right output transducer 608 via a phase/amplitude shifter 610 coupled to the HMD until no sound (or minimal sound) is perceived at the right ear of the wearer. For instance, the wearer may adjust the phase and/or amplitude of the first pure tone signal 600 until the air-conducted pure tone sound at least substantially masks the other portion of the bone-conducted pure tone sound at the right ear of the wearer. Based on the adjustments to the phase and amplitude of the first pure tone signal 600, the HMD may determine $R_{LR}$ (e.g., crosstalk).

Figure 6D:
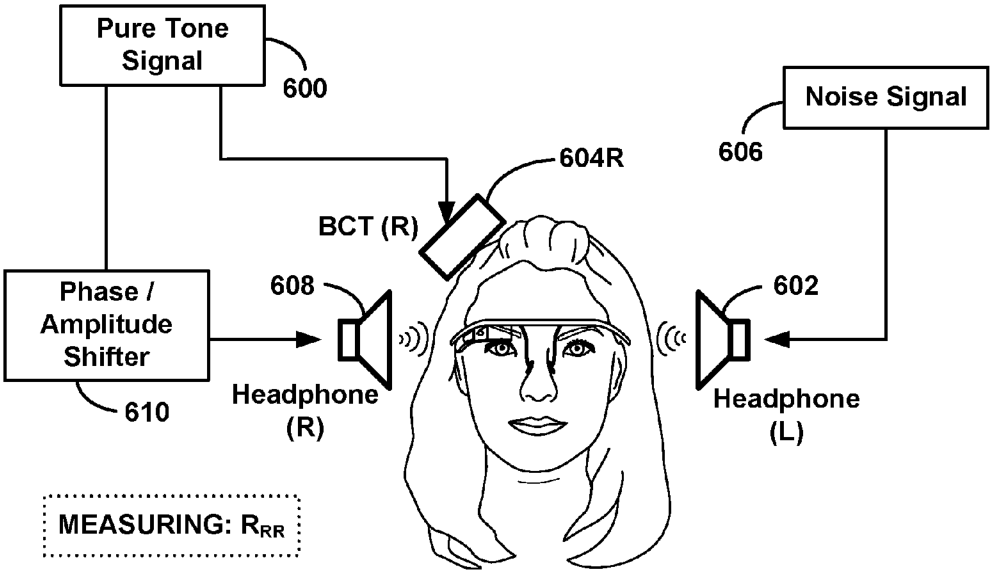

FIG. 6D illustrates a simplified system for measuring in-head response $R_{RR}$. To measure $R_{RR}$, the HMD may transmit a first pure tone signal 600 to a right ear of the wearer via the right output transducer 608 that is coupled to the HMD. The transmitting may be effective to provide an air-conducted pure tone sound to the right ear of the wearer.

The HMD may also transmit a second pure tone signal 600 to the right ear of the wearer. The transmission of the second pure tone signal 600 may be effective to cause a right BCT 604R to vibrate so as to provide a portion of a bone-conducted pure tone sound to the right ear of the wearer and another portion of the bone-conducted pure tone sound (e.g., crosstalk sound) to the left ear of the wearer.

Furthermore, substantially simultaneous to the HMD transmitting the first pure tone signal 600, the HMD may transmit a noise signal 606 to the left ear of the wearer via a left output transducer 602. The noise signal 606 may be effective to provide a noise to the left ear of the wearer and substantially mask the portion of the bone-conducted pure tone sound at the left ear (due to the right ear being measured) so that the wearer can hear both the air-conducted pure tone sound and the portion of the bone-conducted pure tone sound at the right ear of the wearer without distraction by sound at the left ear of the wearer.

Moreover, while the first and second pure tone signals 600 and the noise signal 606 are being transmitted to the wearer of the HMD, the wearer may adjust the phase and/or amplitude of the first pure tone signal 600 being transmitted by the right output transducer 608 via a phase/amplitude shifter 610 coupled to the HMD until no sound (or minimal sound) is perceived at the right ear of the wearer. For instance, the wearer may adjust the phase and/or amplitude of the first pure tone signal 600 until the air-conducted pure tone sound at least substantially masks the portion of the bone-conducted pure tone sound at the right ear of the wearer. Based on the adjustments to the phase and amplitude of the first pure tone signal 600, the HMD may determine $R_{RR}$.

Figure 7:
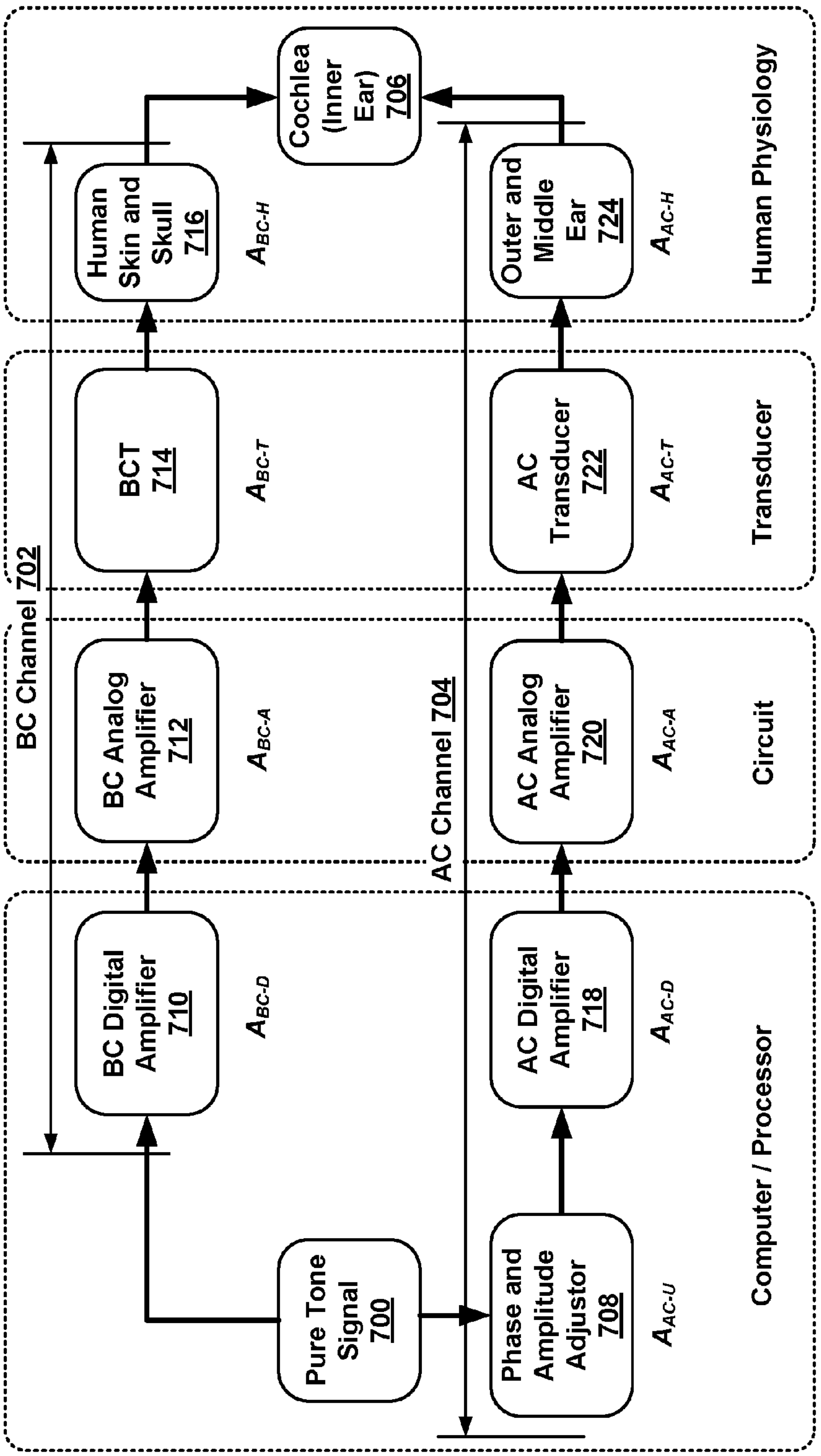
FIG. 7 is a block diagram of a more detailed system for measuring a transform, in accordance with at least some embodiments described herein.

FIG. 7 is a block diagram of a more detailed system for measuring the transform $\vec{T}$ described herein. For an HMD to measure a given in-head response value ($R_{XY}$), a pure tone signal 700 may be fed into both a bone conduction channel 702 and an air conduction channel 704 such that both a bone-conducted sound and an air-conducted sound are perceived by the wearer of the HMD at the wearer's cochlea 706. Further, as noted above, the wearer may use an interface such as a phase and amplitude adjustor 708 coupled to the HMD to adjust the phase and amplitude of the pure tone signal 700 fed into the air conduction channel 704 such that the air-conducted sound substantially cancels the bone-conducted sound at the cochlea 706.

The bone conduction channel 702 may include components such as a bone conduction digital amplifier 710, a bone conduction analog amplifier 712, a BCT 714 for converting the pure tone signal 700 into the bone-conducted sound, and the wearer's human skin and skull 716 (e.g., wearer-specific parameters). Each component of the bone conduction channel 702 may include a respective response, $A_{BC-X}$, which can be measured by the HMD or may be predetermined (e.g., measured in a laboratory or factory). $A_{BC-X}$ may be a vector transfer function that includes both a respective phase and a respective amplitude.

The air conduction channel 704 may include components such as the phase and amplitude adjustor 708, an air conduction digital amplifier 718, an air conduction analog amplifier 720, an air conduction transducer 722, such as a headphone or an earphone, and an outer and middle ear 724 of the wearer. Each component of the air conduction channel 704 may include a respective response, $A_{AC-X}$, which can be measured by the HMD or may be predetermined. $A_{AC-X}$ maybe a vector transfer function that includes both a respective phase and a respective amplitude.

In the example system shown in FIG. 7, the response associated with the wearer's skin and skull 716, $A_{BC-H}$, may represent a given in-head response value, $R_{XY}$. In some examples, each of the responses may be predetermined and may have known values except for $A_{BC-H}$ (which is being measured) and $A_{AC-U}$ (which is adjustable by the wearer). The response $A_{AC-U}$ may then be adjusted until the air-conducted sound substantially cancels the bone-conducted sound (i.e., when the sum of all the responses of the system is equal to zero, as shown in Equation 11). The HMD can then determine $A_{BC-H}$, as shown in Equation 12. $A_{BC-H}$ may be a vector summation of the other responses and may include both a respective phase and a respective amplitude.

$$A_{AC-U}+A_{AC-D}+A_{AC-A}+A_{AC-T}+A_{AC-H}+A_{BC-D}+A_{BC-A}+A_{BC-T}+A_{BC-H}=0 \quad \text{Equation (11)}$$

$$A_{BC-H}=-(A_{AC-U}+A_{AC-D}+A_{AC-A}+A_{AC-T}+A_{AC-H}+A_{BC-D}+A_{BC-A}+A_{BC-T}) \quad \text{Equation (12)}$$

In some examples, the measurement process as described with respect to FIGS. 6A-7 may be applied multiple times for a given in-head response value and the average may be taken. For instance, each measurement of the multiple measurements may be performed with a different pure tone signal frequency. Other examples are also possible.

In some examples, the transform can be calibrated/determined for each unique wearer of the HMD. In other examples, the transform may be an average of a plurality of transforms, each corresponding to a particular wearer. Other examples are also possible.

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A head-mountable device (HMD), comprising:

at least one output transducer;

a plurality of bone conduction transducers (BCTs) including a first BCT proximate to a first side of a head of a wearer of the HMD and a second BCT proximate to a second, opposite side of the head of the wearer;

at least one processor; and data storage comprising instructions executable by the at least one processor to cause the system to perform functions comprising:

transmitting, via the at least one output transducer, a first pure tone signal to a first ear of the wearer, wherein the transmitting provides an air-conducted pure tone to the first ear;

transmitting a second pure tone signal to cause vibration of the plurality of BCTs, wherein the vibration provides a first portion of a bone-conducted pure tone to the first ear and a second portion of the bone-conducted pure tone to a second ear of the wearer;

transmitting, via the at least one output transducer, a noise signal to the second ear, wherein the transmitting provides a noise to the second ear and substantially masks sound at the second ear;

based on wearer-specific parameters, receiving an adjustment of the first pure tone signal such that the adjusted first pure tone signal, when transmitted, provides the air-conducted pure tone and substantially masks the bone-conducted pure tone;

determining a transform based at least in part on the adjustment of the first pure tone signal, wherein the transform is representative of (i) an in-head crosstalk signal path from the second BCT to the first ear, (ii) an in-head crosstalk signal path from the first BCT to the second ear, (iii) a direct signal path from the first BCT to the first ear, and (iv) a direct signal path from the second BCT to the second ear; and using the transform and the plurality of BCTs to perform ambient noise cancellation at the HMD.

2. The HMD of claim 1, wherein the plurality of BCTs includes at least one piezoelectric BCT, and wherein the at least one output transducer includes headphones configured to provide sound to an outer ear of the first ear and a middle ear of the second ear.

3. The HMD of claim 1, wherein transmitting the noise signal to the second ear comprises continuously transmitting the noise signal.

4. The HMD of claim 1, wherein the adjustment comprises one or more of an adjustment of an amplitude of the first pure tone signal and an adjustment of a phase of the first pure tone signal.

5. The HMD of claim 1, wherein the wearer-specific parameters include wearer-specific mechanical-acoustical parameters based on at least a bone composition of a skull of a wearer of the HMD and a tissue composition of a head of the wearer.

6. The HMD of claim 1, further comprising at least one input transducer, wherein using the transform and the plurality of BCTs to perform ambient noise cancellation at the HMD comprises:

receiving, by the at least one input transducer, a first audio signal associated with ambient sound from an environment of the HMD;

processing the first audio signal so as to determine a second audio signal that is out of phase with the first audio signal and effective to substantially cancel at least a portion of the first audio signal;

multiplying a superposition of the second audio signal and a third audio signal by the transform to generate a noise-cancelling audio signal, wherein the third audio signal is representative of a sound to be provided by the HMD; and based on the noise-cancelling audio signal, causing a given BCT of the plurality of BCTs to vibrate so as to provide, to an ear of the first and second ears, a noise-cancelling sound representative of the noise-cancelling audio signal and effective to substantially cancel at least a portion of the ambient sound.

7. The HMD of claim 6, wherein providing to the ear the noise-cancelling sound is further effective to provide, to another ear of the first and second ears, a portion of the noise-cancelling sound, wherein the at least one processor includes a crosstalk cancellation processor configured to generate a crosstalk cancellation signal representative of a crosstalk-cancelling sound to be provided by the plurality of BCTs, and wherein the crosstalk-cancelling sound is effective to substantially cancel the portion of the noise-cancelling sound.

8. The HMD of claim 6, wherein the at least one input transducer includes one or more microphones coupled to the HMD.

9. The HMD of claim 6, wherein the second audio signal includes an anti-phased audio signal that is about 180 degrees out of phase with the first audio signal.

10. A method comprising:

transmitting, via at least one output transducer of a head-mountable device (HMD), a first pure tone signal to a first ear of a wearer of the HMD, wherein the transmitting provides an air-conducted pure tone to the first ear;

transmitting a second pure tone signal to cause vibration of a plurality of bone conduction transducers (BCTs) of the HMD, wherein the vibration provides a first portion of a bone-conducted pure tone to the first ear and a second portion of the bone-conducted pure tone to a second ear of the wearer, wherein the plurality of BCTs includes a first BCT proximate to a first side of a head of the wearer of the HMD and a second BCT proximate to a second, opposite side of the head of the wearer;

transmitting, via the at least one output transducer, a noise signal to the second ear, wherein the transmitting provides a noise to the second ear and substantially masks sound at the second ear;

based on wearer-specific parameters, receiving an adjustment of the first pure tone signal such that the adjusted first pure tone signal, when transmitted, provides the air-conducted pure tone and substantially masks the bone-conducted pure tone;

determining a transform based at least in part on the adjustment of the first pure tone signal, wherein the transform is representative of (i) an in-head crosstalk signal path from the second BCT to the first ear, (ii) an in-head crosstalk signal path from the first BCT to the second ear, (iii) a direct signal path from the first BCT to the first ear, and (iv) a direct signal path from the second BCT to the second ear; and using the transform and the plurality of BCTs to perform ambient noise cancellation at the HMD.

11. The method of claim 10, wherein the adjustment comprises one or more of an adjustment of an amplitude of the first pure tone signal and an adjustment of a phase of the first pure tone signal.

12. The method of claim 10, wherein the wearer-specific parameters include wearer-specific mechanical-acoustical parameters based on at least a bone composition of a skull of a wearer of the HMD and a tissue composition of a head of the wearer.

13. The method of claim 10, wherein the plurality of BCTs are configured to contact the wearer at one or more locations when in use, and wherein the one or more locations include: a location proximate to a condyle of the wearer, a location proximate to a mastoid of the wearer, and a location proximate to a temple of the wearer.

14. The method of claim 10, wherein using the transform and the plurality of BCTs to perform ambient noise cancellation at the HMD comprises:

receiving, by at least one input transducer of the HMD, a first audio signal associated with ambient sound from an environment of the HMD;

processing the first audio signal so as to determine a second audio signal that is out of phase with the first audio signal and effective to substantially cancel at least a portion of the first audio signal;

multiplying a superposition of the second audio signal and a third audio signal by the transform to generate a noise-cancelling audio signal, wherein the third audio signal is representative of a sound to be provided by the HMD; and based on the noise-cancelling audio signal, causing a given BCT of the plurality of BCTs to vibrate so as to provide, to an ear of the first and second ears, a noise-cancelling sound representative of the noise-cancelling audio signal and effective to substantially cancel at least a portion of the ambient sound.

15. A non-transitory computer readable medium having stored thereon instructions that, upon execution by a head-mountable computing device (HMD), cause the HMD to perform functions comprising:

transmitting, via at least one output transducer of the HMD, a first pure tone signal to a first ear of a wearer of the HMD, wherein the transmitting provides an air-conducted pure tone to the first ear;

transmitting a second pure tone signal to cause vibration of a plurality of bone conduction transducers (BCTs) of the HMD, wherein the vibration provides a first portion of a bone-conducted pure tone to the first ear and a second portion of the bone-conducted pure tone to a second ear of the wearer, wherein the plurality of BCTs includes a first BCT proximate to a first side of a head of the wearer of the HMD and a second BCT proximate to a second, opposite side of the head of the wearer;

transmitting, via the at least one output transducer, a noise signal to the second ear, wherein the transmitting provides a noise to the second ear and substantially masks sound at the second ear;

based on wearer-specific parameters, receiving an adjustment of the first pure tone signal such that the adjusted first pure tone signal, when transmitted, provides the air-conducted pure tone and substantially masks the bone-conducted pure tone;

determining a transform based at least in part on the adjustment of the first pure tone signal, wherein the transform is representative of (i) an in-head crosstalk signal path from the second BCT to the first ear, (ii) an in-head crosstalk signal path from the first BCT to the second ear, (iii) a direct signal path from the first BCT to the first ear, and (iv) a direct signal path from the second BCT to the second ear; and using the transform and the plurality of BCTs to perform ambient noise cancellation at the HMD.

16. The non-transitory computer readable medium of claim 15, wherein using the transform and the plurality of BCTs to perform ambient noise cancellation at the HMD comprises:

receiving, by at least one input transducer of the HMD, a first audio signal associated with ambient sound from an environment of the HMD;

processing the first audio signal so as to determine a second audio signal that is out of phase with the first audio signal and effective to substantially cancel at least a portion of the first audio signal;

multiplying a superposition of the second audio signal and a third audio signal by the transform to generate a noise-cancelling audio signal, wherein the third audio signal is representative of a sound to be provided by the HMD; and based on the noise-cancelling audio signal, causing a given BCT of the plurality of BCTs to vibrate so as to provide, to an ear of the first and second ears, a noise-cancelling sound representative of the noise-cancelling audio signal and effective to substantially cancel at least a portion of the ambient sound.

17. The non-transitory computer readable medium of claim 16, the functions further comprising:

receiving, by the at least one input transducer, a fourth audio signal associated with another ambient sound from the environment of the HMD;

processing the fourth audio signal so as to determine a fifth audio signal that is out of phase with the fourth audio signal and effective to substantially cancel at least a portion of the fourth audio signal;

multiplying a superposition of the fifth audio signal and a sixth audio signal by the transform to generate another noise-cancelling audio signal, wherein the sixth audio signal is representative of another sound to be provided by the HMD; and based on the other noise-cancelling audio signal, causing another given BCT of the plurality of BCTs to vibrate so as to provide, to another ear of the first and second ears, another noise-cancelling sound representative of the other noise-cancelling audio signal and effective to substantially cancel at least a portion of the other ambient sound.

18. The non-transitory computer readable medium of claim 17, wherein the second audio signal includes an anti-phased audio signal that is about 180 degrees out of phase with the first audio signal, and wherein the fifth audio signal includes an anti-phased audio signal that is about 180 degrees out of phase with the fourth audio signal.

19. The non-transitory computer readable medium of claim 17, wherein, based on the transform, the noise-cancelling audio signal is effective to substantially cancel at least a portion of the other noise-cancelling audio signal, and wherein, based on the transform, the other noise-cancelling audio signal is effective to substantially cancel at least a portion of the noise-cancelling audio signal.

20. The method of claim 1, wherein the first side of the head is a left side of the head, wherein the first BCT is proximate to the left side of the head, wherein the first ear is a left ear on the left side of the head, wherein the second side is a right side of the head, wherein the second BCT is proximate to the right side of the head, and wherein the second ear is a right ear on the right side of the head.

* * * * *